(12) United States Patent
Dirix et al.

(10) Patent No.: US 8,285,026 B2
(45) Date of Patent: Oct. 9, 2012

(54) METHOD AND SYSTEM FOR USE IN INSPECTING AND/OR REMOVING UNSUITABLE OBJECTS FROM A STREAM OF PRODUCTS AND A SORTING APPARATUS IMPLEMENTING THE SAME

(75) Inventors: Bert Dirix, Tienen (BE); Dirk Adams, Tongeren (BE); Pieter Op De Beeck, Kortenaken (BE)

(73) Assignee: VISYS NV, Hasselt (BE)

( * ) Notice: Subject to any disclaimer, the term of this patent is extended or adjusted under 35 U.S.C. 154(b) by 574 days.

(21) Appl. No.: 12/450,449

(22) PCT Filed: Mar. 27, 2008

(86) PCT No.: PCT/EP2008/053689
§ 371 (c)(1),
(2), (4) Date: Sep. 25, 2009

(87) PCT Pub. No.: WO2008/116924
PCT Pub. Date: Oct. 2, 2008

(65) Prior Publication Data
US 2010/0046826 A1 Feb. 25, 2010

(30) Foreign Application Priority Data
Mar. 27, 2007 (EP) .................................... 07105063

(51) Int. Cl.
*G06K 9/00* (2006.01)
(52) U.S. Cl. .......................................................... 382/141
(58) Field of Classification Search .................. 382/141, 382/143
See application file for complete search history.

(56) References Cited

U.S. PATENT DOCUMENTS

| 6,473,168 | B1 | 10/2002 | Ruymen |
| 6,509,537 | B1 | 1/2003 | Krieg et al. |
| 6,671,042 | B1 * | 12/2003 | Almogy ...................... 356/237.3 |
| 6,864,970 | B1 | 3/2005 | Ruymen et al. |
| 7,557,922 | B2 * | 7/2009 | Adams et al. ................. 356/402 |
| 2005/0052644 | A1 | 3/2005 | Lewis et al. |
| 2007/0030476 | A1 * | 2/2007 | Adams et al. ............... 356/237.1 |

FOREIGN PATENT DOCUMENTS

| EP | 1 724 030 A2 | 11/2006 |
| WO | 01/07950 A1 | 2/2001 |

* cited by examiner

*Primary Examiner* — Roy M Punnoose
(74) *Attorney, Agent, or Firm* — Nath, Goldberg & Meyer; Jerald L. Meyer; Stanley N. Protigal

(57) ABSTRACT

Disclosed is a method and system for inspecting and sorting unsuitable or irregular objects in a stream of products, the system includes means for scanning the stream of products along a scan line. The scan line is formed by means of at least one light source directing light along the scan line, and means for detecting light beams reemitted by the product stream upon scanning. The scanning means includes a focusing means for concentrating the light in at least one dimension. The detecting means includes a focusing means for forming an image in an image plane. The detecting means is oriented towards the scan line such that points on the scan line form a projected scan line in the image plane and the image substantially located in the image plane is substantially focused in at least one dimension by the focusing means. The detecting means also includes a spatial filtering means that filters the image in substantially the direction perpendicular to the direction of the projected scan line.

27 Claims, 14 Drawing Sheets

METHOD AND SYSTEM FOR USE IN INSPECTING AND/OR REMOVING UNSUITABLE OBJECTS FROM A STREAM OF PRODUCTS AND A SORTING APPARATUS IMPLEMENTING THE SAME

This is a National Phase Application filed under 35 U.S.C. 371 as a national stage of PCT/EP2008/053689, filed on 27 Mar., 2008, an application claiming the benefit of European Patent Application 07105063.7, filed on 27 Mar., 2007, the entire content of each of which is hereby incorporated by reference in its entirety.

TECHNICAL FIELD OF THE INVENTION

The present invention relates to a novel method and system for inspecting unsuitable objects or irregularities in a product stream, particularly the invention concerns a method and system for inspection allowing high speed product conveying and a sorting apparatus comprising such system.

BACKGROUND OF THE INVENTION

An apparatus for sorting products provided in a continuous stream is known in the art. Such sorting apparatus comprises a transport system, an inspection system and a removal system. The transport system conveys the product stream to be inspected towards the inspection system and the removal system. The inspection system will analyze one or more predetermined characteristics of the products. Typically optical characteristics such as color and structure are being examined. Based upon the optical signals it receives, the inspection system will evaluate if the measured values of these characteristics for a given object in the product stream meet predetermined acceptance criteria. If not, this object is subsequently removed from the product stream by the removal system. Hereto the inspection system controls the operation of the removal system.

The configuration of such a sorting apparatus is disclosed by U.S. Pat. No. 6,509,537. This sorting apparatus comprises a conveyor for transporting a stream of solid particles and a device for detecting and differentiating between the quality and/or the color of the individual solid particles. The detection system comprises a laser beam, which is redirected towards the solid particles via a polygon wheel. Due to the rotation of the polygonal wheel the mirroring end surfaces of the wheel will azimuthally guide the laser beam in a temporal saw-tooth movement. The moving laser beam is then directed towards the stream of solid particles to provide a linear laser beam scan thereof. The laser beam, which is re-emitted by the solid particles in a divergent way, is redirected via the mirroring end surfaces of the wheel towards photoelectrical devices converting the optical signal into an electrical output signal. The polygon wheel has thus two functions: creating a scanning laser beam over the product stream and redirecting light returning from the product stream to photoelectrical devices. This output signal can then be further handled by analog electrical circuitry or converted into a digital signal for digital processing and data manipulation. Likewise U.S. Pat. No. 4,723,659, U.S. Pat. No. 4,634,881 and European patent application EP 1 332 353 disclose sorting devices comprising inspection systems in which the polygonal wheel has two functions as described above. Such systems include all drawbacks of the prior art due to the fact that scanning means have also the responsibility of re-directing the returning light through detection means, e.g. photomultiplier detectors, thus the systems are strictly bounded with a second function which in turn does not allow to optimize the system in particular for high speed sorting operations.

TR 2006/05534U discloses a similar sorting device configuration as above with the exception that at least one of the detectors is provided with a diaphragm (delimiting device) having a slit like aperture solely for the purpose of tolerating deviations of the incoming light, which deviation is generally caused by improper movement of the scanning means i.e. rotatably arranged polygonal mirror. The present invention provides also, as a side technical effect, a solution for these problems associated with said scanning means simply because inspection systems of the current invention receive reemitted light directly from the product stream instead of receiving the incoming light from such scanning means (e.g. polygonal mirror).

U.S. Pat. No. 6,671,042 B1 discloses an inspection system including a multiple beam laser scanning unit and at least one multiple beam dark field imaging unit. Dark field inspection system is defined as a detector collecting scattered light at an oblique angel $\beta$ which is outside of the convergence angle of the post-scan optical system. The scanning unit generates multiple laser spots and scans them along a surface. The imaging unit separately detects light scattered from each of these multiple spots. Each imaging unit includes collection optics and a photodetector per spot, such that each detector detects the scattered light from only its associated spot. However, the spatial filtering means of the inspection system is located in the focal plane which limits the range of angles of all light directed towards the multiple photodetectors. This is particularly disadvantageous in detecting and inspecting irregular objects in a stream of products because it does not allow to determine from which particular area the light originated.

US-A1-2005/052644 discloses a surface inspection system comprising at least one oblique illumination beam and possibly a second illumination beam in sequence or simultaneously. The filtering means described in the specification filters in the spatial frequency domain requiring the detecting means to be in a very specific constellation as is depicted in FIG. 8. It is clear that the filter in the system is not a filter in the spatial domain, but a filter in the frequency domain of the image. It is therefore that said filter is ideally suited to filter out regular, reoccurring patterns in the image. It is further evident that the Fourier filters employed in the system, also have stringent requirements on the exact locations of the collection lenses in the detection means. That is to say, the object has to be located in the front focal plane of the first collection lens. This system is again not suitable for detecting or inspecting irregular stream of products because it generates an image in the frequency domain as opposed to the spatial domain which is a much more convenient a practical domain in which to define certain window or characteristic functions as used in the present invention and described later in this application.

EP-A-1 724 030 discloses a detection system for inspecting a continuous stream of products comprising a reference element and an intermediate optical element, means for for scanning a light beam over the product stream and means for converting the light beams re-emitted by the product stream into an electrical signal. A polygonal mirror directing the light beam towards the product stream also receives the re-emitted light and directs the same through conversion means. Therefore, scanning means has two functions, namely; directing a light beam towards product stream and receiving/directing the same upon re-emission through detectors. The image formed in said detectors are solely a spot rather than a line.

WO-A-01/07950 discloses a sorting device provided with an inspection unit, a transport system and a rejection unit wherein the inspection unit is provided with at least two light sources and means for having the electromagnetic radiation meet the products. These means function as an alignment system for the radiation originating from said sources. This alignment system simply receives the electromagnetic radiation reflected and/or transmitted and/or emitted and/or transformed by the products to be sorted. However, the system does not allow discrimination of the light scattered and directly re-emitted from the product stream.

To measure scattering effects it is essential in the prior art that the incident light is concentrated in two dimensions, more particularly concentrated as a spot of light. In that case, the image as seen by the detector is made up of two parts, namely a typically bright center spot, usually referred to as the direct reflected light, and surrounding that a cloud having an intensity dependent on the scattering properties of the illuminated object. Filtering out one of those two spatial image components is done by a two dimensional spatial window, for instance a diaphragm with a circular opening having a blinding spot. Further teaching of such diaphragms can be found in the U.S. Pat. No. 4,723,659.

The amount of light received by the photoelectrical devices is determined by the area of the mirroring end surfaces of the polygon wheel which collect light returning from the product stream. If more light is to be received by the inspection system one can either increase the power of the laser beam or increase the dimensions of the mirroring end surfaces resulting in a larger polygon wheel. Both solutions however have a negative impact on the overall cost of the apparatus. Therefore, the prior art inspection systems still need to be improved so as to obtain an inspection system that does no longer require optimization of the scanning elements in accordance with the amount of received light and that does allow implementation of the scanning elements in considerably smaller dimensions.

If the speed at which the products move through the plane of the scanning beam increases, the scanning frequency must increase proportionally in order to have all passing objects scanned with sufficient vertical resolution. In the prior art inspection systems this can be solved by increasing the rotation speed of the polygon wheel or increasing the number of mirroring end surfaces of the polygon wheel. Apart from the cost implications the latter solution will additionally impact the amount of collected light. To overcome that one should increase the polygon wheel even further, which results in even higher costs.

In some applications it may be advantageous to measure the transmittance of an object instead of its reflectance. The prior art systems which collect the returning light by the polygon wheel can only be used in a reflective mode. Light source and detectors are situated at the same side of the product stream and are optically coupled to the product stream by common optical elements (e.g. the polygon wheel) such that a static, de-scanned image of the scanned object is obtained at the detectors. One could position a second polygon wheel and corresponding detectors at the opposite side of the product stream for measuring the transmitted light. However, appropriate alignment of the frequency and phase of the polygon wheel providing the scanning beam with the polygon wheel collecting the transmitted light is extremely difficult to achieve.

Finally, the optical elements of the inspection system are critical and have a large impact on the overall cost of a sorting machine. Hence it needs to be designed with maximum reliability while keeping minimal cost in mind. These design criteria are generally met by keeping optical distances as short as possible, as few as possible degrees of freedom and stable components to obtain a high enough level of optical stability. In the above mentioned prior art systems, however, these goals can be met only to an unsatisfactory degree. To begin with, the reemitted light has to travel over a considerable optical distance and has to pass through a considerable number of optical elements like mirrors and lenses, before finally reaching the detecting means. Furthermore, these optical elements are mounted in mechanical holders fixed on a stabilized base plate. The holder itself can be pitched and yawed to align the laser beam and sometimes moved back and forth to cope, for instance, with chromatic aberrations. It is a complex task to align such optical systems as can be appreciated by a person skilled in the art. Lastly, as outlined above, the prior art systems need to increase the area of the polygonal mirroring end surfaces as much as possible. However, this has a proportional effect on the area of all other optical elements in the optical path towards the detectors, which is in contradiction with the overall design goal.

One could at least theoretically envisage other ways to de-scan and capture light using complex optical setups such as for instance parabolic mirrors. However these solutions would at least partially suffer from the same shortcoming as given above.

Hence there is a need for an apparatus for inspection of products that doesn't suffer from the shortcomings of the prior art. Thus there is a need for a sorting apparatus comprising an inspection system which doesn't suffer from the shortcomings of the prior art. Advantages of the invention will be further disclosed in the rest of the description with reference to the appended drawings as well as to the above drawbacks of the prior art in more detail.

OBJECTS OF THE INVENTION

One of the objects of the present invention is to provide an inspection system to measure the difference between the light that directly reflected/transmitted from an illuminated scene and the light which is diffusely reflected/transmitted by said scene using optical inspection means.

A further object of the present invention is to provide a method and apparatus for scanning and inspecting a stream of products by means of receiving the reemitted light directly from the scene instead of back via the scanning means and such that the dimensions, setup and realization of said scanning means can be optimized with respect to its scanning function only, without affecting the signal/noise ratio of the overall system.

A further object of the present invention is to provide a sorting apparatus for removing unwanted irregularities and/or objects from a stream of products, comprising the aforementioned inspection system, a control circuitry processing the electrical signals from the detection means either alone or in any combination thereof, and a removal unit operated in accordance with the control signals of said control circuitry.

Another object of the present invention is to provide a detection system wherein the requirement to de-scan the observed image by said detecting means is no longer required.

Still another object of the present invention is to provide a detection device having a delimited field of view in the form of a linear, elongated aperture.

SUMMARY OF THE INVENTION

Objects of the invention are realized using an inspection system as disclosed in claim 1 which implements the novel method of claim 24 and which comprises a device according to claim 29. The inspection system is specifically designed for use in a sorting apparatus as disclosed in claim 20 for sorting a product stream. The system comprises means for statically or periodically scanning the stream of products along a scan line wherein said scan line is formed by means of at least one light source directing light along said scan line, and the system additionally comprises means for detecting light beams reemitted by the product stream upon scanning. Such scanning detecting means are well known in the art as per mentioned above.

The invention is characterized by the fact that said scanning means comprises a focusing means for focusing the reemitted light in at least one dimension, and said detecting means comprises focusing means for forming an image in an image plane wherein said detecting means being oriented towards said scan line such that points on said scan line form a projected scan line in said image plane and said image being substantially focused in at least one dimension by said focusing means. The detection further comprises spatial filtering means filtering said image in substantially the direction perpendicular to the direction of said projected scan line in the spatial domain.

A sorting apparatus employing the above described inspection system enables to modify the scanning means of the prior art machines so as to obtain the components of said scanning means in relatively smaller dimensions. The novel method and configuration also provides to inspect a product stream at relatively high product flow rates due to the fact that the need for directing the reemitted light upon scanning via scanning means (de-scanning) as traditional in the prior art is completely eliminated. Further it allows detecting reflected and/or transmitted light simply by positioning the detector at the same or opposite side of the scanning means.

DETAILED DESCRIPTION OF THE INVENTION

Figure 1A:
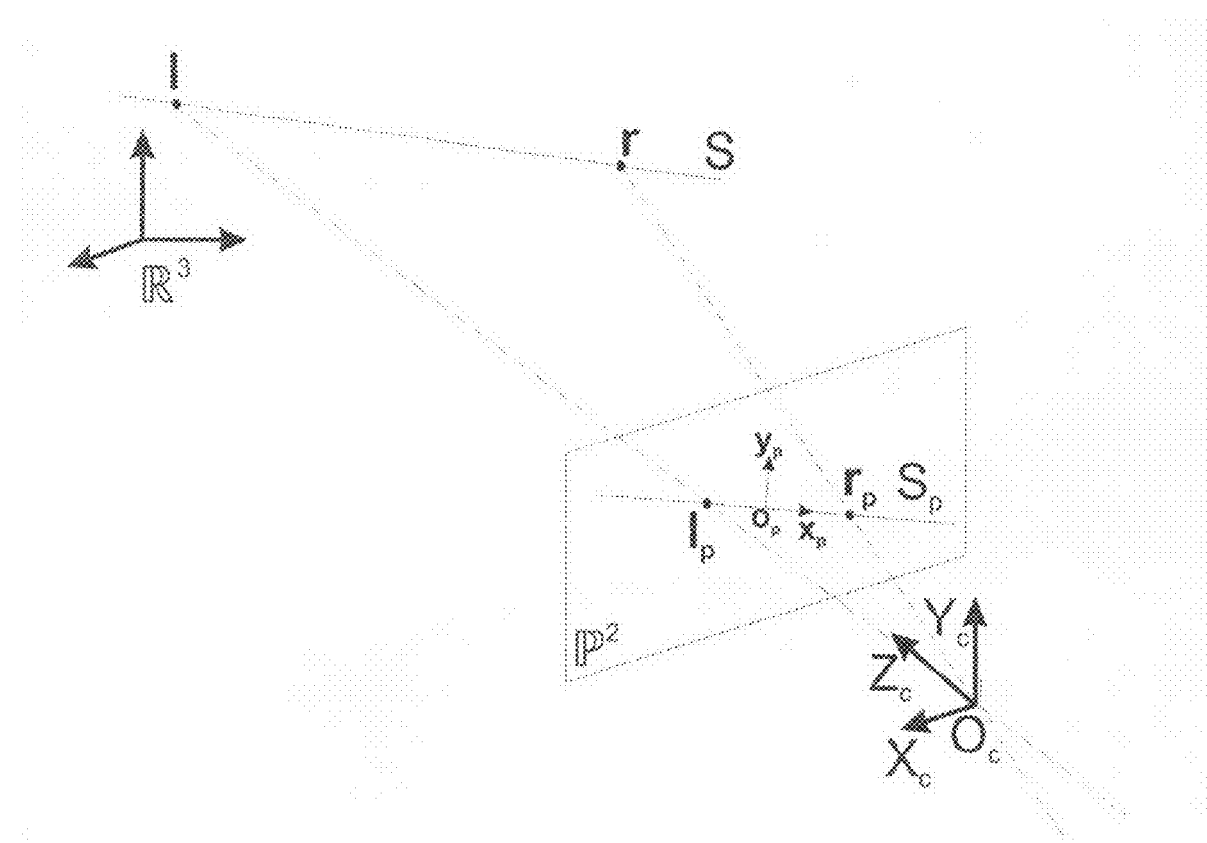
FIG. 1a illustrates the common pin-hole model of a detection system, further introducing the relevant coordinate systems.

The present invention will be further described with respect to exemplary embodiments and with reference to certain drawings but the invention is not limited thereto. The drawings described are only schematic and are non-limiting. In the drawings, the size of some of the elements may be exaggerated and not drawn on scale for illustrative purposes. Hence the dimensions and the relative dimensions do not necessarily correspond to actual reduction to practice of the invention. It is intended that the embodiments and figures disclosed herein be considered illustrative rather than restrictive.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein. For example "underneath" and "above" an element indicates being located at opposite sides of this element.

Further, the term "reemitted" refers to any emitted light, upon impingement of scanning light beams over the scanned product stream, either reflected from or transmitted through said scanning means.

Like elements are referred using like labels.

The embodiments of the present invention disclose an inspection system comprising a scanning means and a detecting means. The inspection system according to these embodiments is of particular use in an apparatus for sorting products which are supplied in a continuous stream. Such inspection system is of particular use for inspecting and sorting not only granular products such as raisins and blueberries but also pellets e.g. plastic pellets, based on optical characteristics such as color and structure. The present invention is not limited to granular products but is also of use for inspecting planar products such as paper, glass plates, e.g. windows, etc.

In general a detection system can be modeled in a coordinate system $[X_c, Y_c, Z_c; O_c]$, where $O_c$ is the centre of projection of said detector, as is depicted in FIG. 1a. An imaging plane $P^2$ can be chosen on which the observed scene is projected. This imaging plane $P^2$ substantially coincides with the image plane of focus. In a first order approximation the scan line S maps to $S_p$ using a perspective projection through $O_c$.

It is well known that in order to make calculations linear, $P^2$ can be interpreted as a projective plane of dimension two embedded in a three-dimensional vector space $R^3$, but it is not an essential step in the current invention.

An orthogonal basis $(x_p, y_p)$ can be defined in the affine plane $P^2$ such that one direction $x_p$ is along the projected scan line $S_p$, and the other direction $y_p$ is perpendicular to $S_p$.

Figures 1B, 1C:
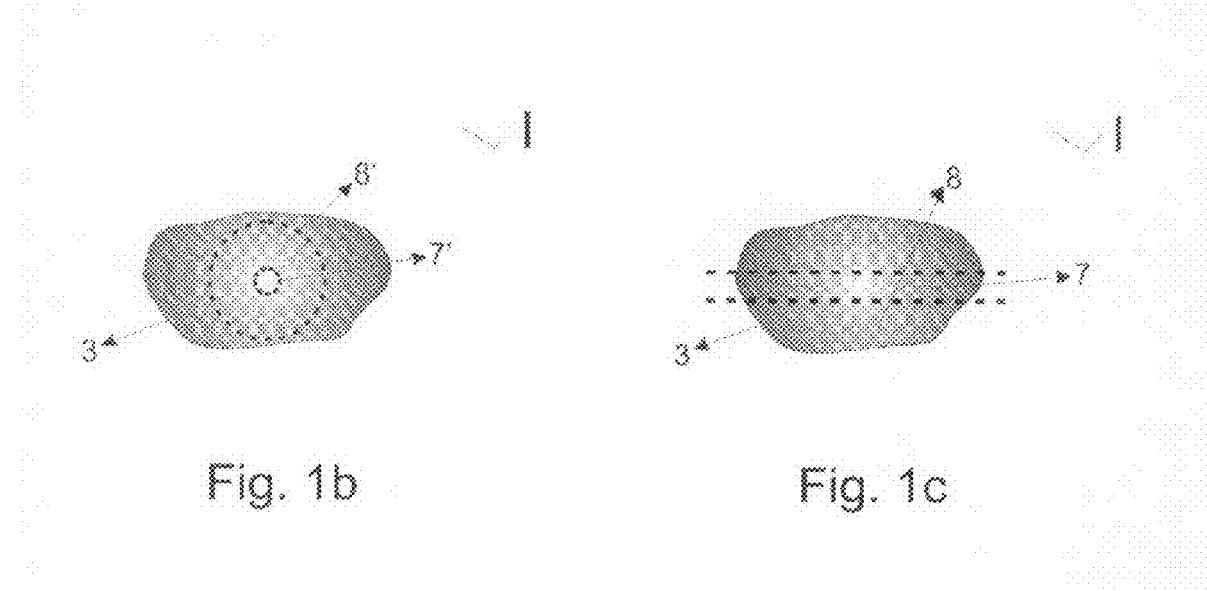
FIG. 1b illustrates the optical effects in an object resulting from illuminating this object with a concentrated light beam.
FIG. 1c illustrates the regions measured by the current invention.

In FIG. 1b an image I is depicted of an object particle 3 that is illuminated by a concentrated light beam. The goal of the invention is to measure the difference between the light 7' that directly reflects/transmits from the illuminated scene 3 and the light 8' which is diffusely reflected/transmitted by said scene 3. Contrary to the prior art, where this difference is measured in all spatial directions, the current invention is predicated by the realization that some of the directions, more particular the direction $x_p$ along said projected scan line $S_p$, can be ignored while still being able to measure said difference with a sufficient degree of accuracy. In that respect we define the region 7 depicted in FIG. 1c which represents predominantly the directly reemitted light and the region 8 which is representative for the scattered light.

This in the past unanticipated trade-off enables embodiments having a clear benefit over the existing prior art. This will be further elaborated on and exemplified throughout the remainder of the present description. In any case, to exploit said new property it is required by the current invention that means are operatively put in place to spatially filter said projected scene in $P^2$ in only the direction $y_p$ perpendicular to said projected scan line $S_p$.

As an example, a scanning means and a detection means focused in the two planar dimensions $x_p$ and $y_p$ are considered. To scan the full width of the product stream, the focused light is directed towards a rotating polygon wheel with mirroring end surfaces which azimuthally guides the beam in a temporal saw-tooth movement across said product stream producing said scan line S. Contrary to the prior art no de-scanning (receiving the returning light via scanning means and re-directing the same towards the detection means) is performed, therefore, the resulting image captured by the detection means will be a light spot moving swiftly across the projected scan line $S_p$. The scattering effects cannot be observed in the direction along $S_p$. To filter out for instance the directly reemitted light and keep the scattered light information in the direction perpendicular to $S_p$, one could use the window $$w(y_p) = \begin{cases} 0, & |y_p| < \frac{H_2}{2} \\ 1, & |y_p| \geq \frac{H_2}{2}, \end{cases}$$

where $H_2$ is the width of the window, more specifically substantially the width of the directly reemitted light projected on $P^2$. It can be readily verified that the window function w is one-dimensional, in essence only specified in the direction $y_p$ perpendicular to said projected scan line $S_p$. In general, the filtered image F then becomes $$F(x_p, y_p) = I(x_p, y_p) w(y_p),$$

in which I represents the incoming image projected on $P^2$.

Other combinations are feasible between the number of dimensions ($d_i$) in which the incident light is focused and the number of dimensions ($d_r$) in which the returned light is focused. It is however advantageous that both $d_i > 0$ and $d_r > 0$. Embodiments where $d_i = 0$, more particularly those using a diffuse illumination, will not be able to make a difference between scattered and other reflected light without using dark-field illumination techniques often used in microscopy. In other embodiments where $d_r = 0$, more particularly those without an objective focusing means of some sort, there is no spatial relationship between the image points and the observed scene. In that case one can only measure the overall amount of returned light. Nevertheless, the current invention enables much more combinations than what is possible in the prior art where there is the restriction $d_i = d_r = 2$.

For the purpose of teaching the invention in some figures more than one temporal snapshot is shown in one drawing. This gives the added benefit to visualize within one drawing the effect of temporally scanning the product stream. It will be indicated when such a drawing technique is used.

Figure 2:
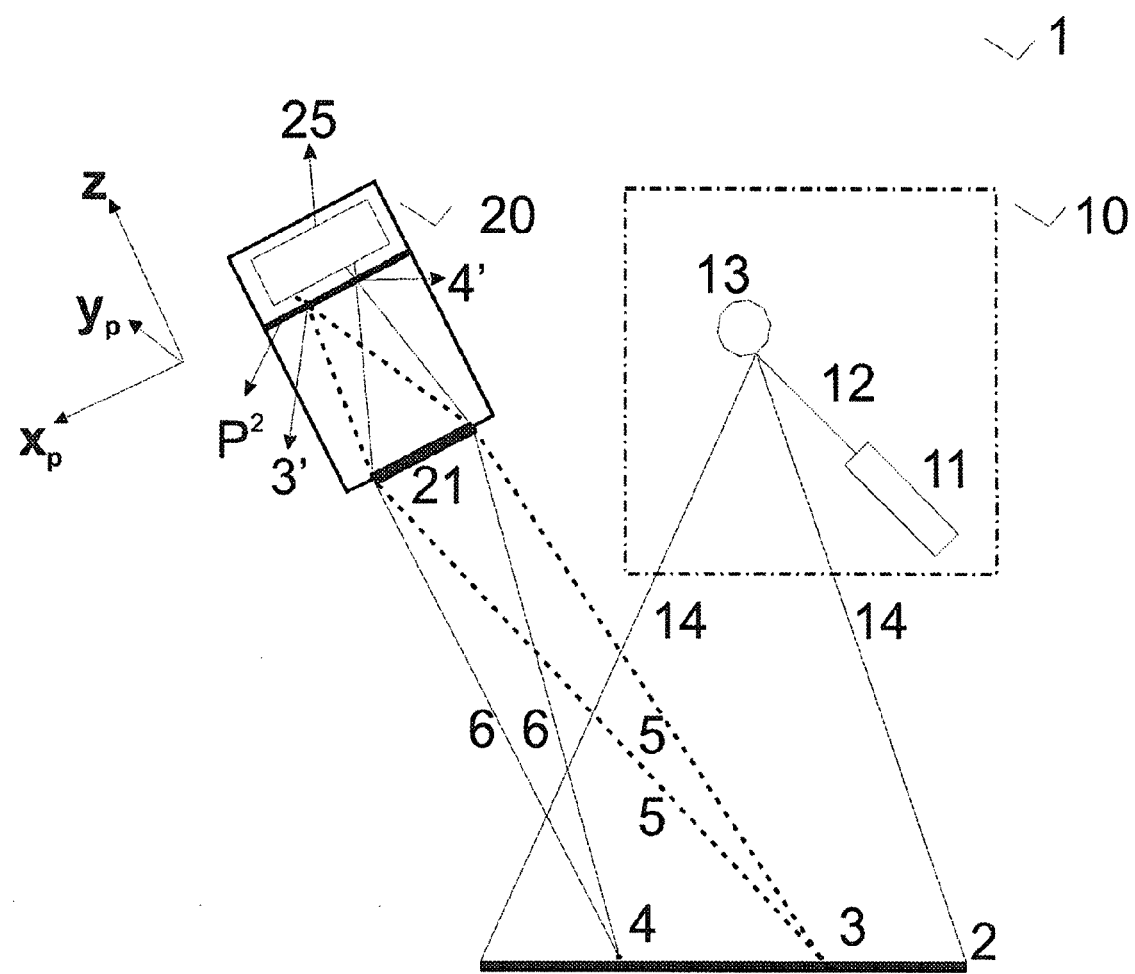
FIG. 2 illustrates an inspection system according to an embodiment of the invention, whereby the reflectance of an object is measured.

FIG. 2 illustrates an inspection system 1 according to a first embodiment. The inspection system 1 comprises means for scanning 10 a concentrated beam 12 over the product stream 2, further comprising means 11 to generate said concentrated beam 12 and means 13 to azimuthally guide said beam 12 in a temporal saw-tooth movement across said product stream 2; means for detecting 20 light beams 5, 6 reemitted by the product stream 2 upon scanning. Said returned light 5, 6 is collected by the detecting means 20 without being reflected or otherwise interfered with by the scanning means 10. In other words the light path 5, 6 reemitted by the product stream 2 towards said detecting means 20 is optically separated from the incident light path 14 towards said product stream 2. This embodiment therefore does not suffer from the shortcomings of the prior art systems because the scanning means 10 can be dimensioned independently from the detecting means 20, more particularly the dimensions of the polygon wheel 13 need only optimization with respect to the scanning performance. For example, in the current invention the minimum area of each mirroring end surface of the polygon wheel 13 can be as low as the minimum spot size obtainable by the light source 11 without affecting the signal/noise ratio of the detected light 5, 6. Therefore the polygon wheel 13 can be made considerably smaller than achievable in the prior art, allowing higher rotational speed and higher scanning frequency and a higher vertical resolution than achievable in the prior art. In some applications, like tobacco leafs, where the product flows can be as much as 18 m/s, the inspection system 1 according to the invention can provide satisfactory results with sufficient vertical resolution.

For the purpose of teaching the invention the previously introduced coordinate system $[x_p, y_p]$ associated with the projection plane $P^2$ is illustrated as well. Furthermore $P^2$ is embedded in $R^3$ by introducing the third dimension z, perpendicular to $P^2$. The impingement points 3, 4 are illuminated at different time instances but shown in the same drawing. This is to illustrate that contrary to the prior art, the image I of the moving light spot, formed by focusing means 21, is not being de-scanned and thus the points 3, 4 project onto $P^2$ at different coordinates 3', 4'. To measure the difference between the directly reemitted light 7 and the scattered light 8, a one-dimensional window w is required, spatially filtering said image I in $P^2$ in the direction $y_p$ perpendicular to said projected scan line $S_p$.

The detecting means 20 comprises, in operation, conversion means 25 for converting the detected optical signals 5, 6 into an electrical signal. The thus obtained electrical signals are representative for predominantly the light 7 being directly reemitted and/or the light 8 being scattered from an area surrounding the impingement point or a combination thereof.

Figure 3:
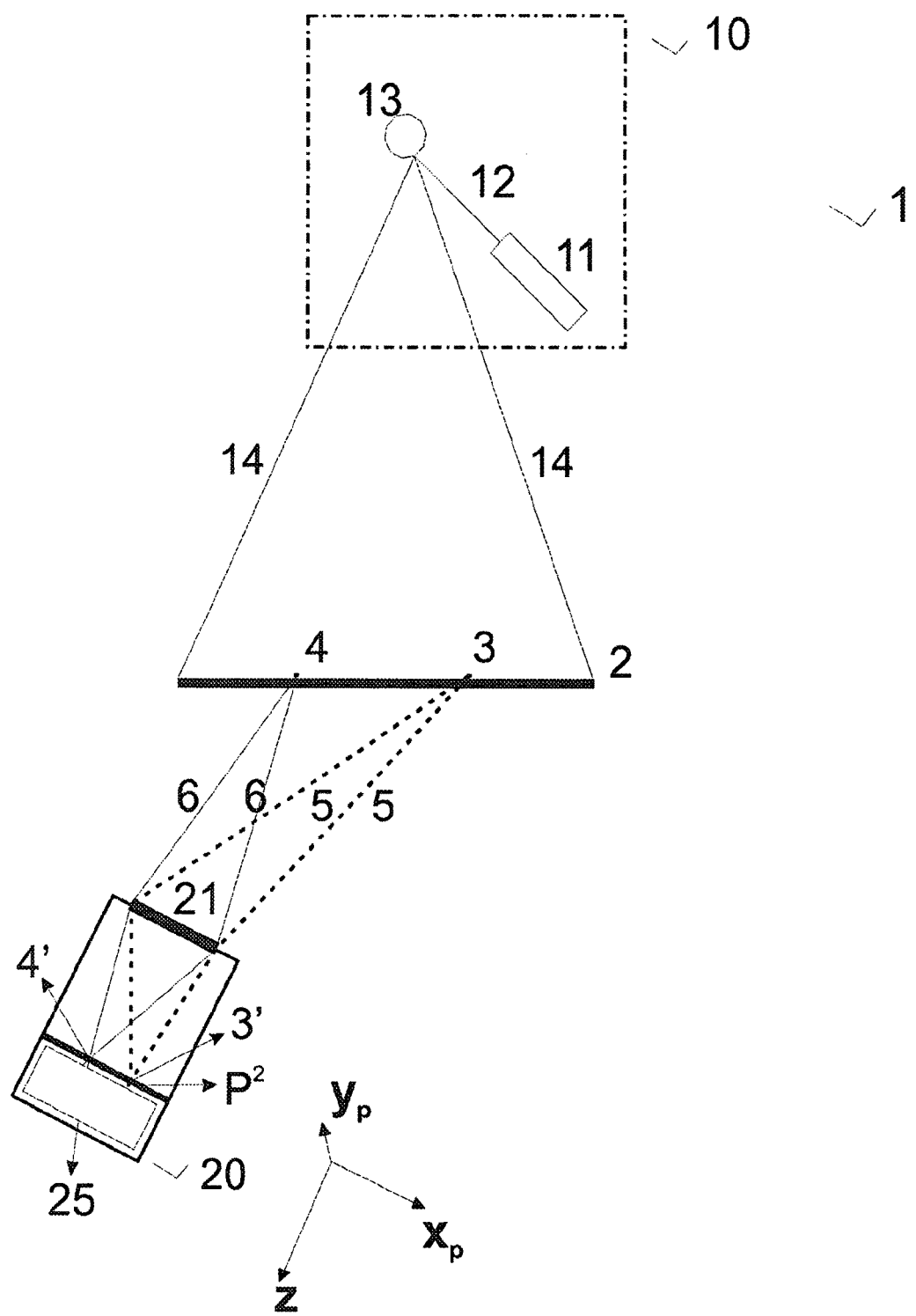
FIG. 3 illustrates an inspection system according to an embodiment of the invention, whereby the transmittance of an object is measured.

FIG. 3 illustrates an inspection system 1 according to a second embodiment. The inspection system 1 comprises means for scanning 10 a concentrated beam 12 over the product stream 2, means for detecting 20 light beams 5, 6 reemitted by the product stream 2 upon scanning.

In this embodiment the detecting means 20 and the scanning means 10 are positioned at opposite sides of the product stream 2. The configuration according to FIG. 3 thus allows detecting transmitted light using the same scanning means 10 and detecting elements 20 as in the embodiment illustrated in FIG. 2, thereby illustrating the flexibility of the disclosed inspection system 1 over the systems disclosed in the prior art. This embodiment is of particular use when translucent or transparent objects are to be inspected. These translucent or transparent objects can be granular products such as food particles, e.g. raisons, non-food particles, such as pellets. These objects can also be planar objects such as translucent or transparent plates, e.g. glass plates, plastic plates. The embodiment illustrated by FIG. 3 allows inter alia inspection of glass plates such as windows for defects or undesired objects incorporated in or on the glass plates, e.g. air bubbles in the glass plate or in foils attached to the glass plate or in the coatings. The translucent or transparent plates are provided to the scanning means in the form of a stream. Typically a plate is being rejected if a predefined number of defects or undesired objects are detected within the scanned area of the plate. Alternatively defect areas, sections or strips are marked and successively cut out and rejected.

An inspection system 1 according to embodiments of the invention can have one light source 11 and multiple detecting means 20 located at different sides of the product stream such that with one scanning light beam 14 directly reemitted light, scattered light, all the light and transmitted light can be detected for each scanned object 3.

In the embodiments illustrated by FIGS. 2 and 3 the scanning effect was obtained by projecting a light beam 12 towards a polygon mirror 13 that rotates. However the scanning effect can be obtained by other means. The movable mirror 13 need not be a mirror that rotates, but can be a mirror element of a configurable optical mirror array (not shown). The position of such mirror and hence the angle at which the concentrated beam 12 is reflected towards the product stream can be varied by applying electrostatic forces to the mirror elements. Such mirror arrays are known in the art and are for example used in optical switches, maskless lithography and digital cinema, displays or television. Typically these mirror arrays are fabricated as a Micro-Electro-Mechanical-System (MEMS) using fabrication processes known from semiconductor technology. Such MEMS devices are provided amongst other by SAMSUNG or by Texas Instruments, where it is known as DLP® (Digital Light Processing Technology). The concept of digital micro-mirror arrays is disclosed amongst others by Jack Younse in "Mirrors on a chip", in IEEE volume 30, issue 11 Nov. 1993, page(s) 27-31. The concept of an optical scanner using micro-mirrors is for example disclosed in published United States application US 20060023284. In any case, such scanning means 10 cannot be used in the prior art because it does not allow for the second function, more particular the function of detection and de-scanning of the image I.

Figure 4A:
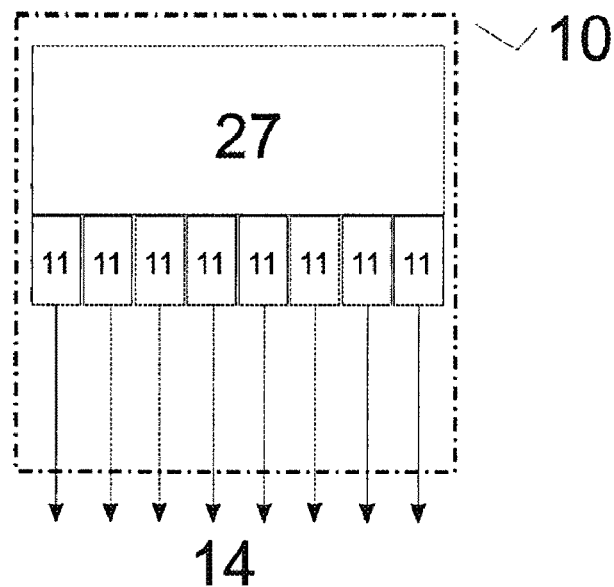
FIG. 4a illustrates a scanning means which is an array of multiple light sources according to an embodiment of the present invention. Each individual light source can be ignited sequentially, one after the other or permanently.

The scanning effect in embodiments according to the invention can be obtained by means other than mirrors as illustrated in FIG. 4a,b. An advantage of the present invention is that light originating from the scanned products need not be reflected by the same mirror providing the scanning effect. Hence the scanning means 10 are only to provide a scanning light beam 14 and not to collect light 5, 6 originating from the product stream 2. Contrary to the prior art the scanning means 10 can be used for generating a scanning light beam 14 only.

Figure 4B:
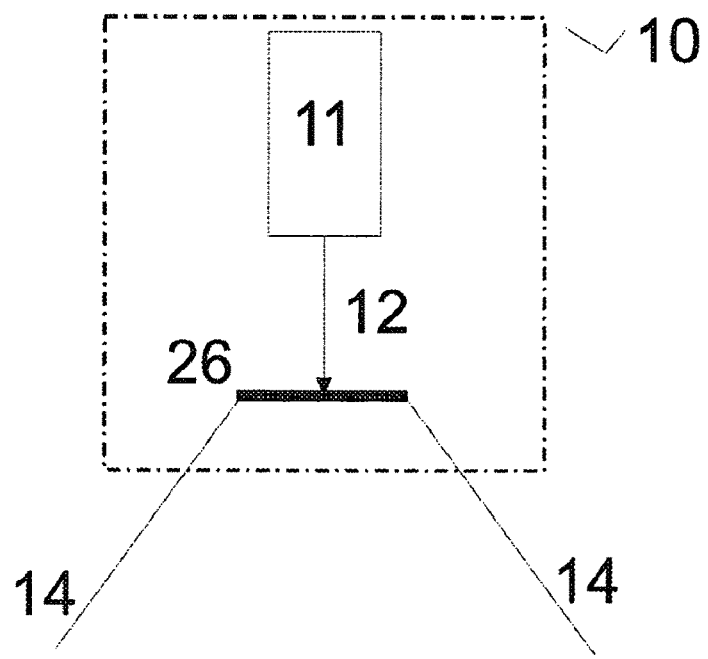
FIG. 4b illustrates a scanning means which provides a static concentrated light sheet over a scan line according to an embodiment of the invention.

For example, the scanning means 10 can be a light source 11 that rotates, which upon rotation, provides a laser beam 14 moving over the product stream 2. The scanning means 10 can be an array of light sources 11, such as laser sources, e.g. laser diodes or any other source providing a concentrated light beam such as a collimated and focused light source, which are operatively arranged to provide scanning of the product stream 2, as illustrated in FIG. 4a. Various ways exist to control 27 an array of light sources 11 as to provide a scanning effect. The relative phases of the individual light beams 12 emitted by the respective light sources 11 can be varied in such a way that a light pattern of the array is reinforced in a desired direction and suppressed in other directions. Such phased array can thus be used to provide a scanning light beam 14. Alternatively, if the light sources 11 are arranged in a linear array, electronic control circuitry 27 can be provided to sequentially ignite the individual light sources 11 one after another such that successive light spots are generated on the product stream. In another preferable embodiment the individual light sources 11 can be ignited permanently whereby a static scan line is produced. Preferably the linear array is designed to cover the complete width of the product stream 2 such that all passing objects can be scanned. In FIG. 4b focusing means 26 are explicitly shown in optical connection with the light source 11 generating a static sheet 14 of concentrated light in one dimension. A diffuse light source 11 can direct light 12 towards such means 26 which can be a collimater in combination with a converging cylindrical lens, or alternatively a laser beam generator 11 can be directed towards such means 26 which in this case can for instance be a grating. Still another way to generate a static scan line is to use a projector or beamer, a well known device to project images, projecting an image of a line (not shown). Such scanning means 10 are of particular use for the detection of defects in situations where these defects need only to be detected up to the time when they occur and not up to their exact position along the scan line. A typical example is the inspection of glass coatings or the lack thereof. When such a deficiency is detected either the whole currently inspected glass plate is removed or a complete glass strip is tagged for subsequent removal.

The current invention is however not limited to the embodiments described above and any scanning light beam 14 focused in at least one dimension, more particularly with $d_r>0$ ($d_r$ defined as the number of dimensions in which the incident light is concentrated) falls within the scope of its protection.

A person skilled in the art will realize that more than one light source can be used. The configurations illustrated by FIG. 2, 3, 4a or 4b only employed one light source 11 providing a single light beam 12 of a specific wavelength or within a specific (continuous) wavelength range. In some applications it might be advantageous to scan the product stream 2 with more than one light beam 14 or to be able to choose between different light beams available. Each light beam has a different wavelength or (continuous) range of wavelengths. The respective wavelengths are selected in function of the products to be scanned, in particular in function of their response to and/or sensitivity to the scanning light beam as function of the wavelength. For example the product stream can be simultaneously scanned with an infrared and a green light beam. Other applications would require other combinations of wavelengths, as will be appreciated by a person skilled in the art.

Figure 5:
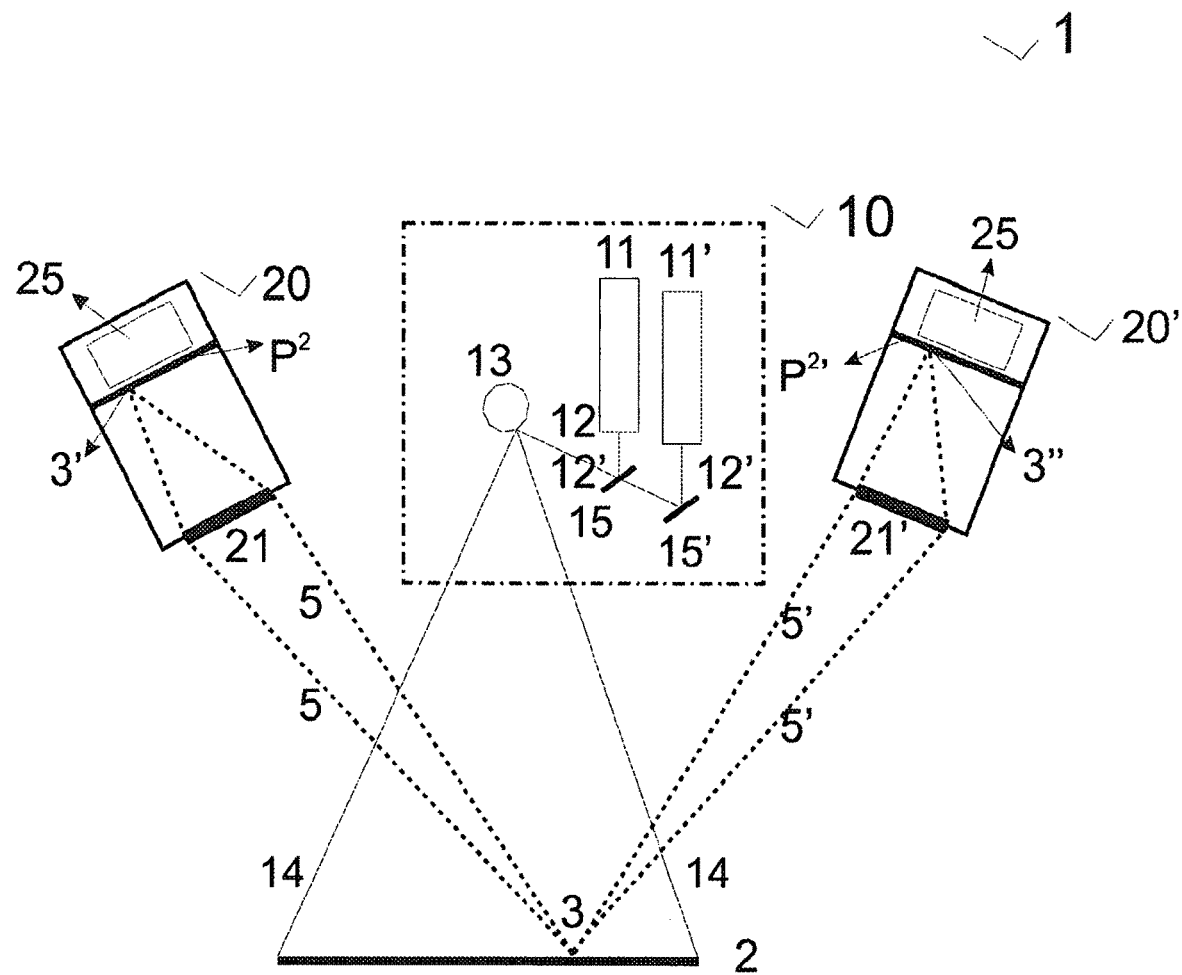
FIG. 5 illustrates an inspection system comprising multiple scanning beams and multiple detecting means according to an embodiment of the invention.

FIG. 5 illustrates such a configuration of an inspection system 1 comprising multiple light sources 11, 11' for generating multiple light beams 12, 12'. In such configuration, shown in FIG. 5, the light beam 12, 12' of each light source 11, 11' is reflected towards the movable mirror 13 by a semitransparent or dichroic mirror 15, 15' such that light beams 12, 12' hit the movable mirror 13 at substantially the same position and the light beams 14 will scan the product stream 2 in substantially the same plane. Thereto the semitransparent mirrors 15, 15' are aligned along the same optical axis. Each semitransparent mirror 15 reflecting the light 12 from the corresponding light source 11 towards the movable mirror 13, while light 12' reflected from other mirrors 15' along the optical axis is being passed through.

As can be appreciated by the person skilled in the art the position of the detecting means 20 can be freely chosen as scanning means 10 and detecting means 20 are not synchronized to each-other and operate independently from each-other. Contrary to the prior art, the position of the detecting means 20 can thus be selected in view of available space, optimized detection or type of light signals 5 to be detected e.g. reflective or transmissive without impacting the position of the scanning means 10. If multiple detecting means 20, 20' are used, these detecting means 20, 20' can be positioned at the same side of the scanning means 10 or at different sides of the scanning means 10, as illustrated by FIG. 5. The scanning means 10 and the detecting means 20 can be located at the same side of the product stream 2, as illustrated by FIG. 2, or at opposite sides of the product stream 2, as illustrated by FIG. 3. A person skilled in the art will realize that other combinations of detecting means 20 and scanning means 10 can be envisaged, e.g. multiple detecting means 20, 20' positioned opposite the scanning means 10 such that the transmittance of the objects in the product stream 2 at various wavelengths can be measured.

As the product stream 2 is scanned by light beams 14, 14' with different wavelengths appropriate detecting means 20, 20' need to be foreseen. Preferably the number of detecting means 20, 20' equals at least the number of scanning light beams 14, 14' such that each detecting means 20, 20' can be selected to be sensitive to a different wavelength. More preferably the number of detecting means 20, 20' exceeds the number of scanning light beams 14, 14', whereby the detecting means tuned to the same wavelength are sensitive to different regions (i.e. scattered region and/or directly reemitted region) in the image I formed. Each detecting means 20 can have different parameter settings (e.g. gain, offset, etc.) and its operation can be optimized independently from the other detecting means 20'.

Figure 6:
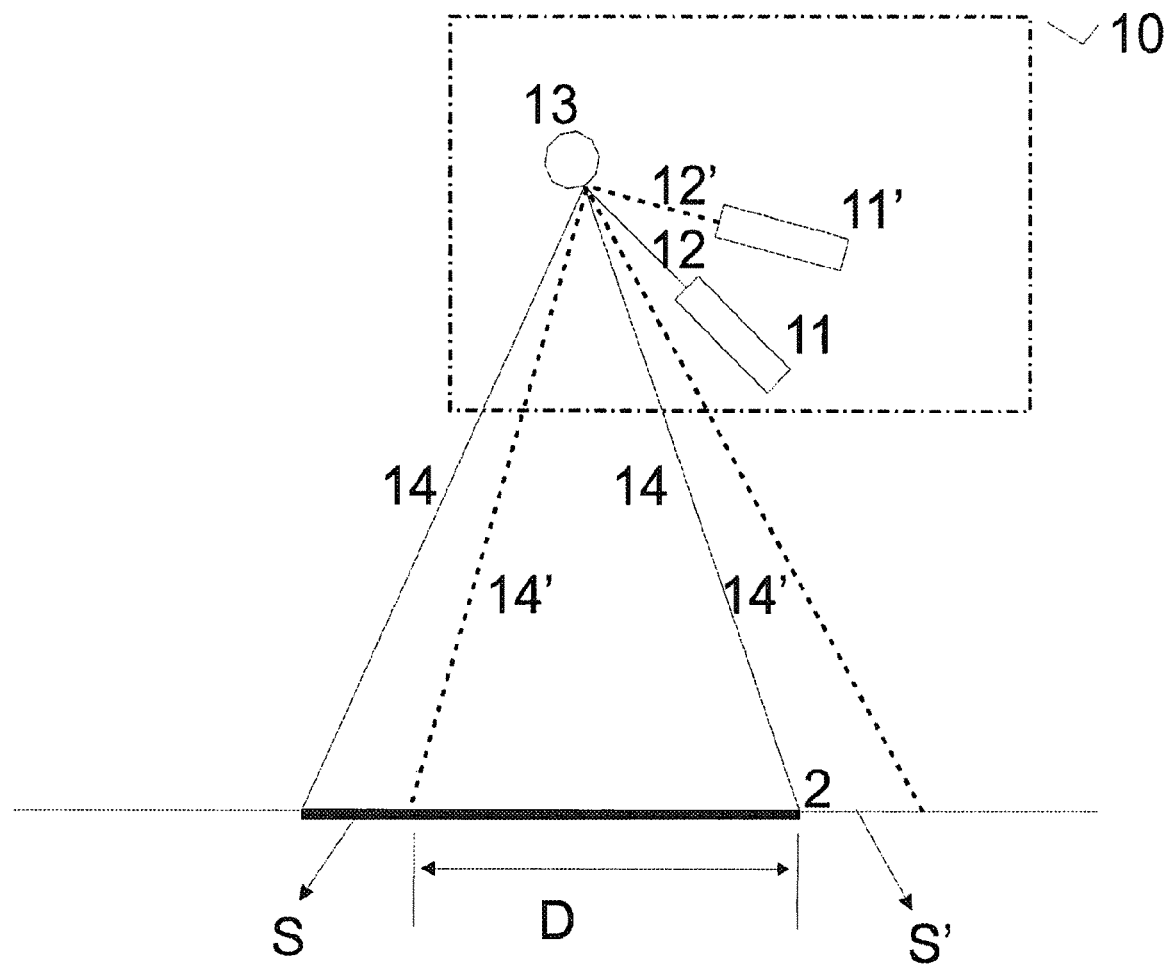
FIG. 6 illustrates an inspection system comprising multiple scanning beams oriented at different angles towards the movable mirror according to an embodiment of the invention.

Whereas in the embodiment illustrated by FIG. 5 the individual light beams 12, 12' are directed towards the movable mirror 13 along the same optical axis, one can direct the light beams 12, 12' along different optical axes to the movable mirror 13, thereby avoiding the use of dichroic mirrors 15, 15' to align the individual light beams 12, 12'. The individual light beams 12, 12' now impinge on the movable mirror 13 under different angles, each light beam 12, 12' upon reflection by the movable mirror 13 providing a scan beam 14, 14' resulting in a scan line S, S' of the same width. The scan lines S, S' of the individual light beams 12, 12' are selected to at least partially overlap such that the overlapping scan lines correspond to the width D of the scanned product stream. This embodiment is illustrated by FIG. 6. In the prior art this optimization is made impossible by the use of a mirror-with-hole which is used to separate the originating light beam from the collected, returned light. The hole in the mirror would have to be made too large.

A person skilled in the art will appreciate that a similar effect can be achieved by positioning each light source 11, 11' under a different spatial angle. In any case, it is clear that these setups cannot be conceived in the prior art.

The inspection system 1 according to embodiments of the present invention allow each light beam 14 to scan the product stream 2 in a separate plane because the scanning means 10 only provide the scanning light beam 14 and need not collect the light 5, 6 returning from the product stream 2. The scanning means 10 and the detecting means 20 are decoupled and operate independently from each-other. Hence scanning means 10 comprising multiple rotating light sources 11, 11' or multiple arrays of light sources 11, 11' such as a linear array of laser diodes are applicable in inspection systems 1 according to embodiments of the present invention.

Instead of having one movable mirror from light source 13 one can choose to have multiple movable mirrors 13, each mirror being operatively linked with a light source 11 (not shown). If for example a configurable optical mirror array is used as disclosed supra, each mirror element in this array can be associated with an individual light source.

In the prior art detection systems the light beam 14 projected towards the product stream 2 and light beams 5, 6 collected from the product stream 2 need to be in the same plane as both pass via common elements of the scanning means. In inspection systems 1 according to the present invention one can choose at what angle the detecting means 20 are placed with respect to the scanning plane, i.e. the plane in which the scanning light beam 14 moves back and forth over the product stream 2.

Figure 7:
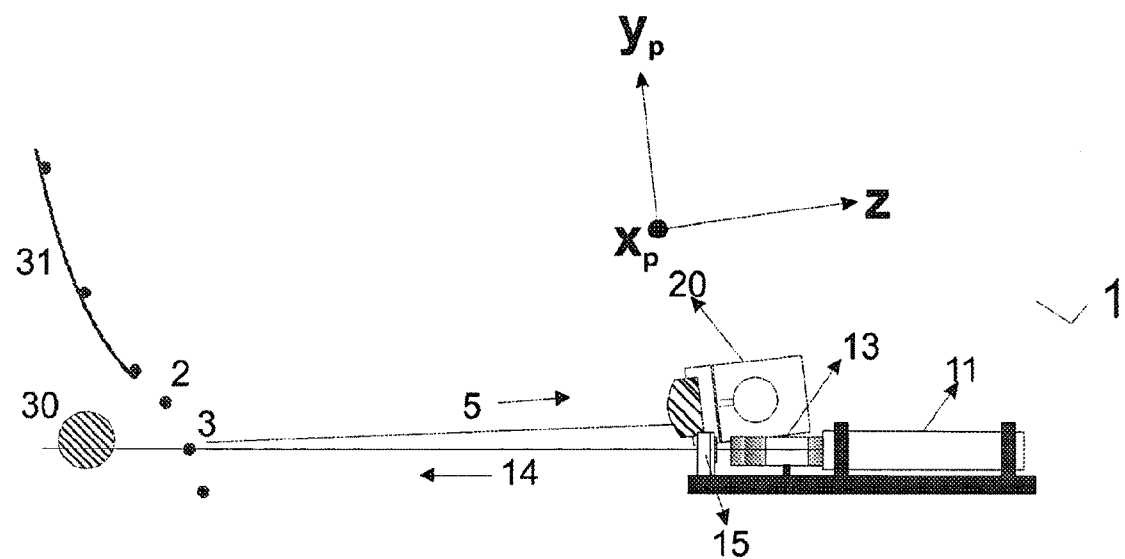
FIG. 7 illustrates an inspection system comprising detecting means positioned at an angle to the optical plane of the scanning light beam according to an embodiment of the invention.

In the configuration illustrated by FIG. 7 the detecting means 20 are positioned at an angle with respect to the scanning means 10. Hence the scanning light beam 14 towards the product stream 2 and the collected light beam 5 returning from the product stream 2 propagate substantially in different planes. If multiple light scanning beams 14, 14' are used the scanning means 10 can be positioned such that corresponding scanning planes are slightly tilted towards each-other. FIG. 7 can be considered as a side view of the FIG. 2 with only one light source 11 and scanning means 10 when looking from the right to left. FIG. 7 further shows a chute 31 for guiding the product stream 2 towards the scanning plane. Behind the product stream 2, i.e. at the side opposite the side where the scanning means is placed, a background element 30 is provided which is used inter alia to calibrate and correct the inspection system 1 and to provide an optical reference.

Optionally the scanning light beam 14 can be directed towards the product stream 2 through a semitransparent window such that the scanning light beam can pass through this semitransparent mirror to impinge upon the product stream. This mirror allows directing the scanning light beam towards the product stream but substantially prevents light beams returning from the product stream to enter the scanning means, in particular the light source, thereby negatively impacting the operation of the scanning means, in particular the light source 11.

Figure 8:
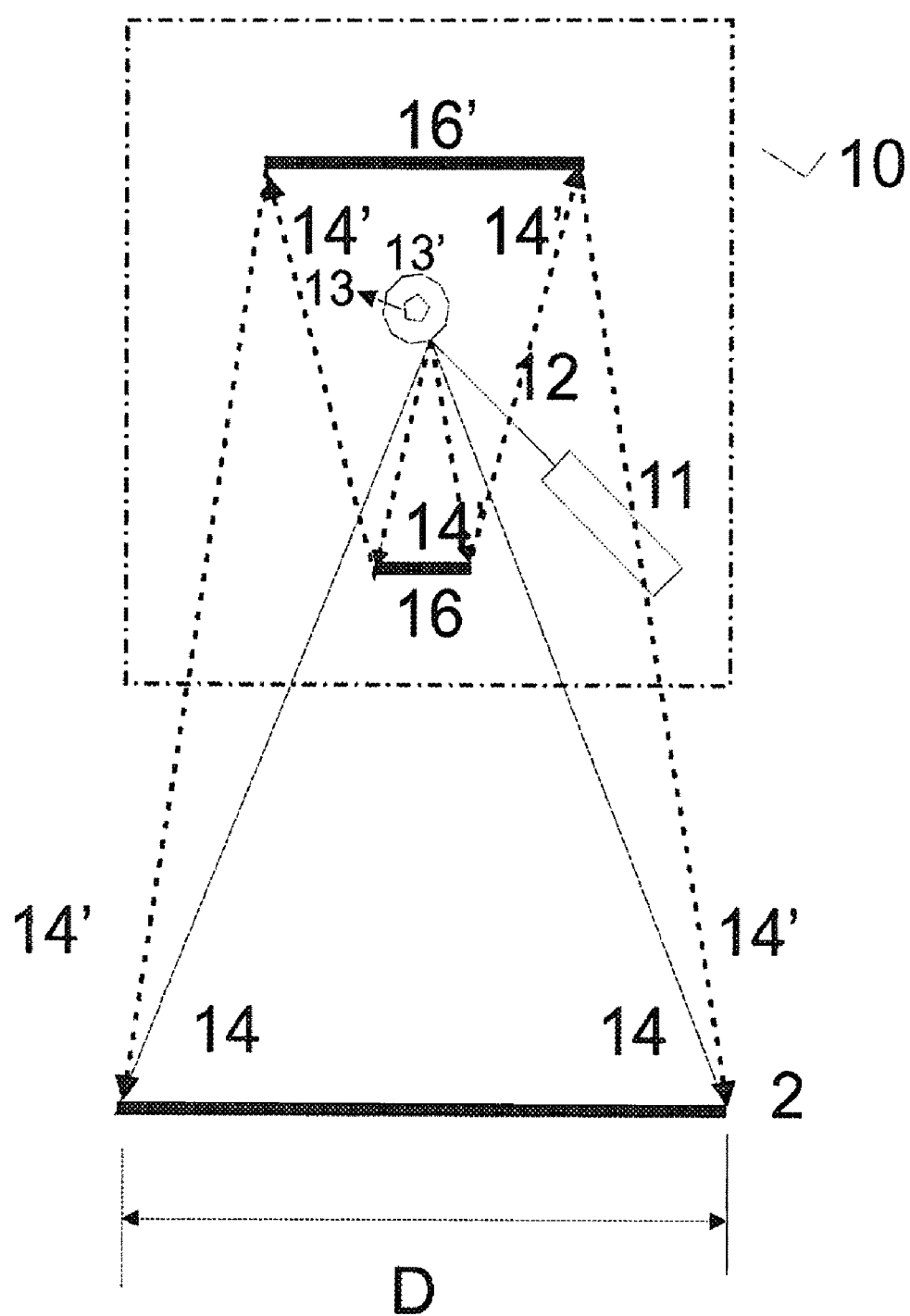
FIG. 8 shows an embodiment illustrating the reduced distance between scanning means and the scanned product stream compared to the prior art for the same scan width D.

FIG. 8 shows an embodiment illustrating the reduced distance between scanning means 10 and the scanned product stream 2 compared to the prior art for the same scan width D. The distance between the rotating polygon wheel 13 and the product stream 2 is kept the same for the prior art configuration and the configuration according to an embodiment of the invention. However, as can be seen in the same FIG. 8 and as explained below the optical distance is significantly reduced.

It can be shown that with polygonal wheels 13 the angle over which the scanning light beam 14 moves is 4π/n; with n the number of mirroring end surfaces. If a rotating polygon wheel 13' according to the prior art is used, the number of mirroring end surfaces for a given dimension of the polygon wheel 13' is limited because the area of each mirror should be sufficiently large to collect sufficient incoming light. To increase the angle over which the polygon wheel scans for a given optical distance to the product stream 2, the number of these mirrors has to be decreased. Unfortunately this will proportionally reduce the scan frequency as well. Because polygonal wheels 13' of the sizes required by the prior art are limited in rotational speed one can therefore not decrease the number of mirrors as much as in the current invention. If a product stream 2 is to be scanned over a width D there is only one remaining parameter: the distance between the polygon wheel and the product stream 2. It must be increased until the scan width D fits within the scan angle of the scanning light beam 14' at the position of the product stream 2. Consequently the spacing between the product stream 2 and the scanning means 10 can be considerably large, for example in current setups it is 1.8 m to obtain a scan width of 1.2 m. In the current invention the detection means 20 is decoupled from the scanning means 10, whereby the same size restrictions for the polygonal facets do not apply anymore and much smaller polygon wheels 13 can be chosen which can rotate at much higher speeds at closer distances.

Prior art solutions to reduce this spacing comprise folding the scanning beams 14'. This approach is illustrated in FIG. 8 where the dotted lines denote the folded scanning light beam 14'. After being reflected by the rotating polygon wheel 13', the scanning light beam 14' is reflected backwards by a first mirror 16 towards a second mirror 16'. This second mirror 16' in its turn reflects the scanning light beam 14' towards the product stream 2 for scanning thereof. The light returning from the product stream 2 upon scanning will follow the same, large, optical path between the rotating polygon wheel 13' and the product stream 2 as indicated by the dotted lines. For the same optical path length and hence for the same spatial spread of the scanning light beam 14', the folding approach allows positioning the scanning means 10 nearer to the product stream 2 compared to the configuration where the light 12 is directly reemitted by the rotating polygon wheel 13' towards to the product stream for scanning 14' thereof. However, as the optical path length remains the same, the energy of the scanning light beam 14' will be distributed over a larger area. To compensate for the reduced light intensity either more powerful light sources 11 or more sensitive conversion means 25 are needed in the prior art.

In an inspection system 1 according to embodiments of the invention, the number of mirroring end surfaces of the rotating polygon wheel 13 can be easily decreased as discussed inter alia in the embodiment illustrated by FIG. 2. As the number of mirroring end surfaces decreases, the scan angle increases. This is illustrated in FIG. 8 by the solid lines 14 denoting the light reflected by a polygon wheel 13 according to embodiments of the invention. For the purpose of teaching the invention the polygon wheel 13 and the product stream 2 are placed at the same position as for a prior art inspection system comprising a folding system 16, 16'. However, the polygon 13 is drawn conciderably smaller to indicate the difference with prior art polygon dimensions. At the position of the product stream 2 the desired scan width D is obtained even for a reduced spacing between the rotating polygon wheel 13 and product stream 2 without any folding mirror configuration. Hence an inspection system 1 according to embodiments of the invention allows obtaining a large scan angle in a limited space and a limited optical distance between the objects to be scanned and the scanning means 10, thus reducing complexity and cost compared to the prior art.

As indicated in the embodiment illustrated by FIG. 2, no static image of the inspected product stream 2 is obtained when focusing means 21 focuses in both planar dimensions $x_p$ and $y_p$. Light beams 5 originating from an object 3 yield an image 3' in $P^2$ at a predetermined position in the detecting means 20. Likewise, light beams 6 originating from an object 4 at another position in the product stream 2 yield an image 4' in $P^2$ thereof. The image 4' of the object 4, however, is projected onto another predetermined position in $P^2$. While the spot of the scanning light beam 14 is displaced along the scan line S over the product stream 2, the corresponding image 3', 4' in $P^2$ is also linearly displaced along the corresponding projected scan line $S_p$, instead of being projected on substantially the same spot, providing a static de-scanned image, as is the case in the prior art. A person skilled in the art will realize that during effective operation only one image at a time is provided and the presentation of both images 3' and 4' in the same drawing is only to illustrate the temporal effect present in the current invention.

The conversion means 25, when present, will receive light at different positions of its active area. For the purpose of teaching the invention both the product stream and the detecting means are shown in frontal view illustrating how light originates from the scanned objects and further illustrating the images 3', 4' obtained. The detecting means 20 comprising the focusing means 21 is shown in top view to illustrate the different embodiments more clearly.

Figure 9:
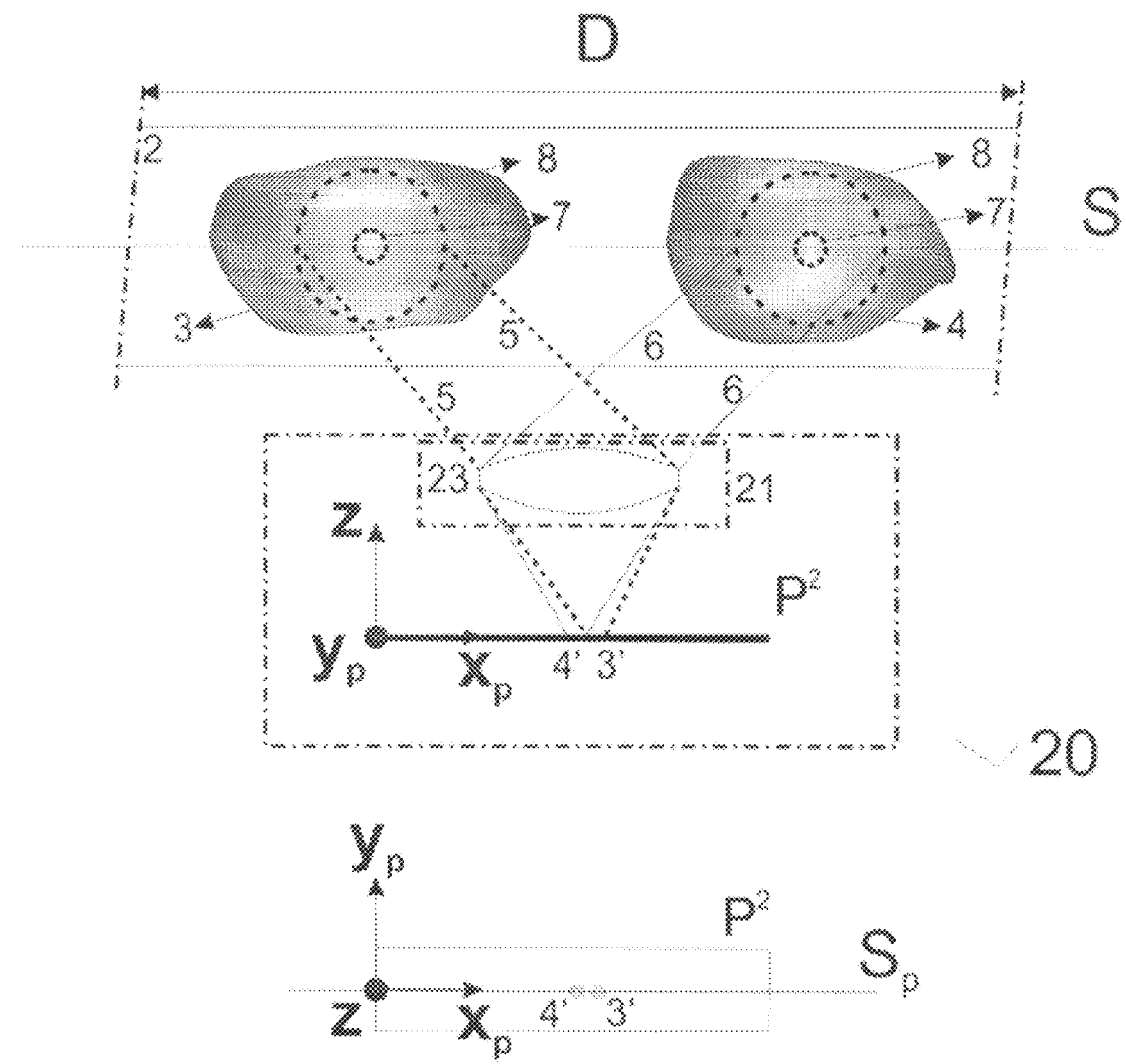
FIG. 9 illustrates focusing means comprising a spherical lens focusing in two perpendicular directions according to an embodiment of the invention.

In the embodiment illustrated in FIG. 9 the light originating 5 from the product stream 2, whether directly reemitted 7 or scattered 8, is focused by means 21 in two dimensions such that an individual image point 3' at an individual predetermined position is formed for each scanned object 3 depending on the position of the object along the scan line S of the scanning light beam 14. The focusing means 21 can be realized with a spherical or aspherical lens 23, more preferably with a converging lens system focusing the reemitted light 5, 6 in two dimensions. The design of such a lens system can be conducted by a person skilled in the art and may incorporate any known design positively impacting the performance of the detecting means 20.

In this embodiment a scan of the scanning light beam 14 over the product stream will result in a linear array of individual images 3', 4' in the detecting means 20; the inner circle corresponding to the detected directly reemitted light 7' and the surrounding circular area corresponding to the detected scattered light 8'. Like regions in the images 3', 4' have like $y_p$ coordinates but varying $x_p$ coordinates. To appreciate at any moment in time the total amount of energy present in the detected light related to the detected directly reemitted light 7' and scattered light 8' a spatial filter w has to be operational in $P^2$ filtering said images 3', 4' in only the direction $y_p$ perpendicular to said projected scan line $S_p$.

Although FIG. 9 demonstrates a situation where the objects 3, 4 are scanned with a concentrated light spot, it was realized that an identical embodiment would yield the same results when illumination was done using a sheet of concentrated light, more particularly an illumination concentrated in only one dimension. When a single light sensitive conversion means 25 is used, for example a photo-multiplier tube, the output signal of said conversion means will only be indicative of the amount of light present in said projected image I and location of the individual objects 3, 4 along S can be recovered. Hence one can only determine the presence of an object 3, 4 along the scan line S. Nevertheless, in some applications this is sufficient, for example when finding coating defects in sheets of glass. In an alternative embodiment the conversion means 25 comprises a matrix of light sensitive elements, for instance a CCD camera chip or an array of photomultiplier tubes, which outputs a digital signal representative of said projected image I in $P_2$. Using well-known image processing techniques the projected scan line $S_p$ can be recovered from said digital image and the exact locations of objects 3, 4 can be extracted, as will be appreciated by a person skilled in the art. In a preferable combination, the windowing function w is implemented in software such that the filtering can be performed on the digitized image.

The focusing means 21 is used to obtain an image 3' of the scanned object 3. As shown in FIG. 9 the image obtained is very small as the ratio between the scanned width D and the width d of the active area of conversion means 25 can be a factor of 100 or more, typically a factor of 150. Likewise the image height along the $y_p$ direction is scaled by the same factor. For example, for a concentrated beam with a cross-sectional diameter of 2 mm (which is typical) the image of the directly reemitted light will be in the order of 15 μm along $y_p$. A diaphragm 22 fully characterized by said spatial filter function w needs to be constructed with mechanical features in the order of micrometers. A person skilled in the art can realize these using techniques as electro-formation, lithography, chrome vaporization on glass and such like.

Figure 10:
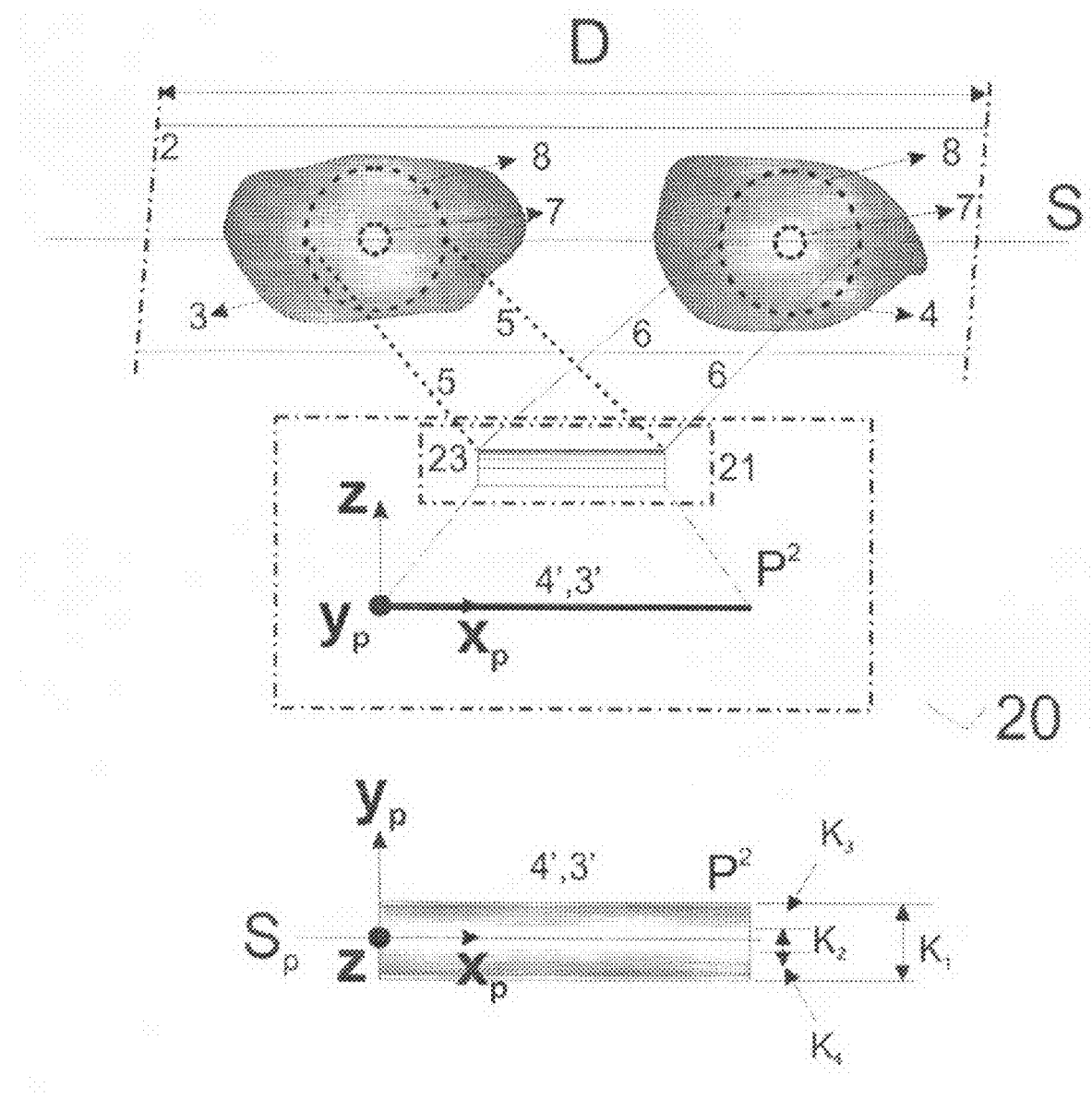
FIG. 10 illustrates focusing means comprising a cylindrical lens focusing in one direction according to an embodiment of the invention.

FIG. 10 illustrates an embodiment wherein the focusing means 21 comprises a converging planar cylindrical lens 23 such that a real image is obtained focused only in the direction $y_p$. More preferably the focusing means 21 comprises a converging lens system focusing the reemitted light 5, 6 in one dimension, more specifically in the direction $y_p$. The design of such a lens system can be conducted by a person skilled in the art and may incorporate any known design positively impacting the performance of the detecting means 20. For the purpose of teaching the invention the images of two scanned objects 3, 4 provided by the detecting means 20 are shown together although in this case the temporal effect is somewhat obfuscated because both objects 3, 4 yield the same striped, overlapping image. A cylindrical lens positioned as shown in FIG. 10 has a vertical magnification, more precisely a magnification along its power meridian, but does not alter the light in the perpendicular direction and are thus particularly useful in inspection systems according to embodiments of the present invention, more particularly the magnification in the $y_p$ direction can be chosen independently from the factor D/d. After passing through said focusing means 21 the collected light beams 5 will be focused and magnified along the power meridian, more accurately along the $y_p$ direction, while in the $x_p$ direction the light beams are not focused resulting in a striped image as depicted in FIG. 10.

In the embodiment illustrated by FIG. 10 each point source 3', 4' will be imaged as three linear bands of energy; the inner linear band or strip corresponding predominantly to the directly reemitted light 7 component of the image of the detected light 5 and has a height $K_2$, the two outer bands at opposite sides of the inner band corresponding to the scattered light 8 component of the image of the detected light 5 and having respective heights $K_3$ and $K_4$. The total height of the image 3 will be $K_1$, which is the sum of $K_2$, $K_3$ and $K_4$. Each point source 3 along the scan line S of the scanned product stream 2 will yield a linear image stripe or strip 3 over the whole active width d of the conversion means 25 instead of a dot at a particular ($x_p$, $y_p$) coordinate. However one can differentiate between images 3', 4' of successive scanned objects 3, 4 by correlating the temporal progress of the scanning beam 14 with the linear image obtained. Each moment in time corresponds to a predetermined position of the scanning spot 14 and hence the energy distribution measured in the detecting means 20 corresponds to the light 5 reemitted by the object 3 at that predetermined position. Alternatively, optical systems other than lenses can be applied to yield the same effect, namely obtaining a linear image of each scanned point 3, for example prism-pairs, mirror pairs and such like as will be appreciated by a person skilled in the art. By selecting the magnification of the focusing means 21 along its power meridian the relative heights $K_2$, $K_3$ and $K_4$ of the different bands can be selected such that one can control the heights of said individual bands.

Although FIG. 10 demonstrates a situation where the objects 3, 4 are scanned with a concentrated light spot, it is equally indicated that an identical embodiment will yield the same striped image when the illumination was done using a sheet of concentrated light, more particularly an illumination concentrated in only one dimension. However, in that case there is no correlation between the temporal progress of the scanning beam 14 and the linear image obtained; more particularly the image in this case will be the sum of the light reemitted by the scan line S over its full width D. Hence one can only determine the presence of an object 3 along the scan line S, but one cannot determine the exact location along S of said object 3. Nevertheless, in some applications, for example in finding coating defects in sheets of glass, this is sufficient.

The aperture of the detecting means 20 according to the embodiment in FIG. 10 is determined by the active area of the light conversion means 25 in combination with the width of the scanning means 21. This size of the focusing means 21 should be chosen accordingly to capture the scan width D. More specifically, the width of the axis meridian of focusing means 21 should be large enough to capture the outer left and right rays originating from the scan line S.

Figure 11:
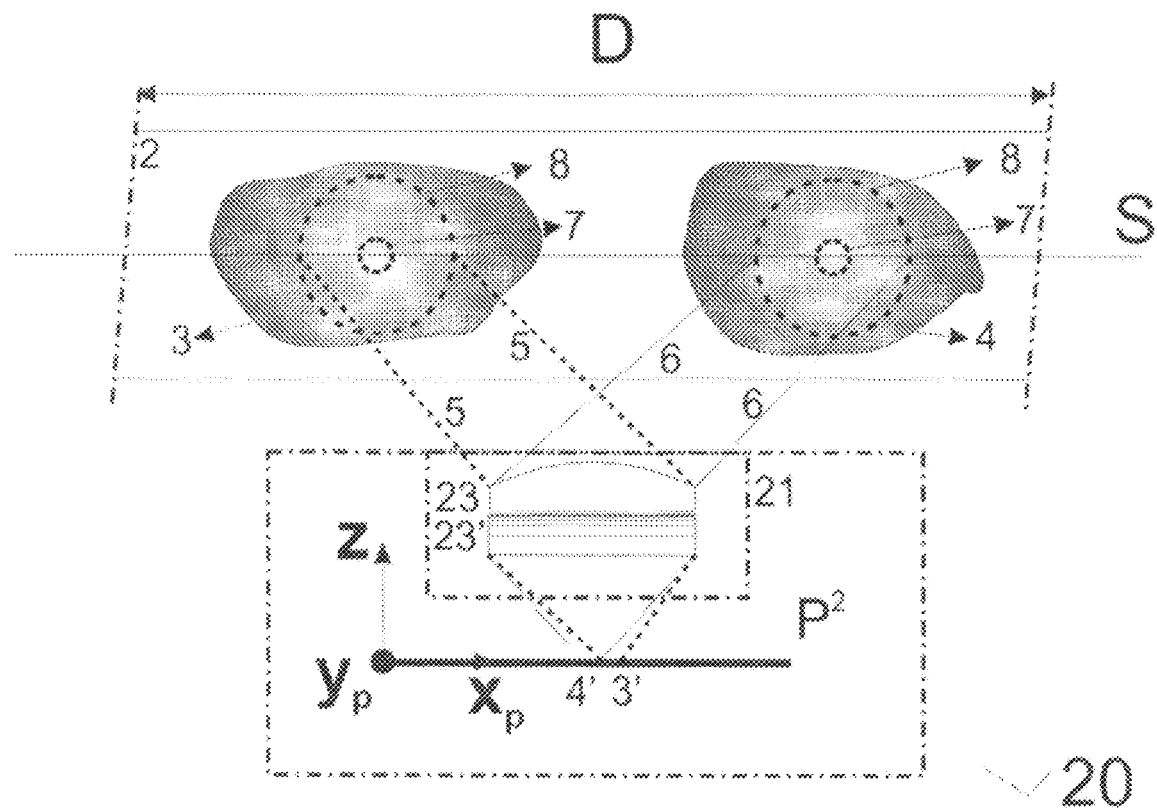
FIG. 11 illustrates focusing means comprising a set of lenses, each lens focusing in one direction according to an embodiment of the invention.
Figure 11:
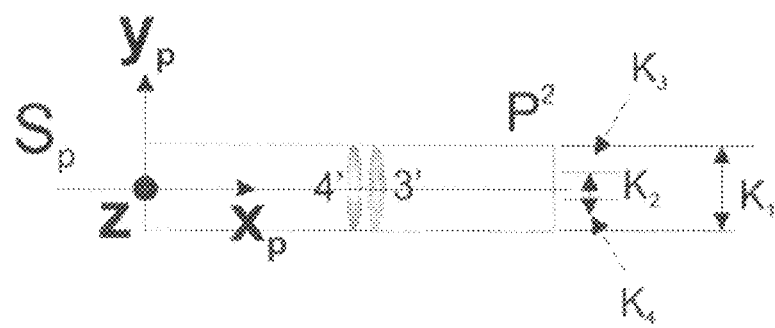

In the embodiment illustrated in FIG. 9 a focusing means 21 was used providing focusing and magnification in both planar directions $x_p$, $y_p$ yielding typical images of each point source 3. FIG. 11 illustrates an embodiment wherein the focusing means 21 comprises a first converging cylindrical lens 23 for focusing in a first direction, i.e. along $x_p$, and a second converging cylindrical lens 23' for focusing in a second direction orthogonal to the first direction, more particularly along $y_p$. The first lens 23 is positioned to direct light beams 5 originating from the product stream 2 towards the second lens 23'. Also here individual images 3', 4' are obtained for each point source 3, 4. However, these images 3', 4' are magnified differently along $x_p$ and $y_p$, resulting in elliptical images. For the purpose of teaching the invention the images of two scanned objects 3', 4' provided by the detecting means 20 are shown together. By selecting the magnification along the focusing directions the relative heights, i.e. along $x_p$ and $y_p$, of the inner $K_2$ and outer $K_3$-$K_4$ ellipse can be selected such that one can control the minimal detectable height $K_2$, $K_3$-$K_4$. Alternatively a combination of a converging spherical lens 23 and magnifying cylindrical lens 23' is used to obtain a linear image. The converging spherical lens 23 providing focusing of the incoming light beams 5 in a point image while the magnifying lens 23' will expand the focused light beams along the power meridian, more particularly along $y_p$. In any case the width of the axis meridian (along $x_p$) of the second focusing means 23' can be reduced considerably, unlike in the embodiment in FIG. 10.

A person skilled in the art will realize that the focusing means are to be optimized not only for focusing and magnification. Other requirements such as spherical or chromatic aberration need to be taken into account when determining the optical performance of the detecting means. In addition any known optical techniques can be applied to further increase the amount of light captured by the detecting means, for example using mirrors positioned in front of the focusing means 21 such that more light is directed towards said focusing means 21. As such the focusing means 21 can comprise any combination of optical elements to correct for any of the above, as can be appreciated by a person skilled in the art.

When sorting products, electrical signals are to be generated proportional to predominantly directly reemitted light 7, scattered light 8, transmitted light or any (captured) light originating from the scanned product 3 and received 5 by the detecting means 20. Optionally electrical signals are generated which are a combination of any of the above light signals, alternatively these combinations can be made after digitization of said electrical signals. An inspection system 1 according to any of the embodiments can thus further comprise control circuitry in operable communication with the detecting means 20 for receiving electrical signals generated by the detecting means 20 in response to light 5 collected by the detecting means 20. The control circuitry will then generate control signals based on individual electrical signal or a combination of any of these electrical signals, i.e. the signals can be manipulated by the control circuitry e.g. being summed, subtracted, multiplied or otherwise processed in any way. The optical signals can thus be separately processed and converted into a control signal.

Depending on which part of the light 5 collected at the detecting means 20 is to be converted into an electrical signal, the inspection system 1 comprises;

detecting means 20 having a field of view such that the detecting means 20 are sensitive to all the light collected by the focusing means 21 in which case essentially all light reaching these detecting means 20 is converted, detecting means 20 having a field of view such that these detecting means 23 are sensitive to predominantly only directly reemitted light 7 in which case predominantly only the directly emitted light is converted, or detecting means 20 having a field of view such that these detecting means 20 are sensitive to substantially only scattered light 8 in which case only the scattered light 8 is converted.

An inspection system 1 can comprise any of these detecting means or any combination thereof. As for example illustrated by FIG. 5, an inspection system 1 can comprise more than one detecting means 20, 20'. Each of these detecting means 20, 20' can be selected to be sensitive to a specific wavelength or range of wavelengths and/or to be sensitive to predominantly directly reemitted light 7, to scattered light 8 or to both.

In a particular embodiment of the invention the inspection system 1 comprises a first detecting means 20 having a field of view such that this detecting means 20 is sensitive to predominantly only directly reemitted light 7 and a second detecting means 20' having a field of view such that this detecting means 20' is sensitive to substantially only scattered light 8. In this configuration the control circuitry can sum the electrical signals corresponding to the converted predominantly directly reemitted light 7 and the converted scattered light 8 to obtain an electrical signal representative to both the directly reemitted light and the converted scattered light. This way three control signals can be generated corresponding to predominantly directly reemitted light 7, scattered light 8 or both.

In another embodiment of the invention the inspection system comprises a first detecting means 20 having a field of view such that this detecting means 20 is sensitive to predominantly only directly reemitted light 7 and a second detecting means 20' having a field of view such that this detecting means 20' is sensitive to both directly reemitted light 7 and scattered light 8. In this configuration the control circuitry can subtract the electrical signals provided by the first 20 and to the second 20' detecting means to obtain an electrical signal representative to substantially only scattered light 8. This way three control signals can be generated corresponding to predominantly directly reemitted light 7, scattered light 8 or both.

As outlined in the previous embodiments the detection means 20 provides an image 3' of each scanned object 3 which will be either a striped image 3' along the projected scan line $S_p$ as illustrated by FIG. 10 or an image 3' moving along the projected scan line $S_p$ in accordance to the scanning of the product stream 2. In the latter case the moving image 3' can be circular as illustrated by FIG. 9 or elliptical as illustrated by FIG. 11.

In either case, part of the image 3' formed in the detecting means relates to detected directly reemitted light 7, while another part relates to the detected scattered light 8. Because of the linear character of said images the circular diaphragms from the prior art can not be used to allow passage of selected parts of each image in order to differentiate between the different components of the detected light, more particular they cannot be characterized by a suitable spatial filtering function w.

Figure 12A:
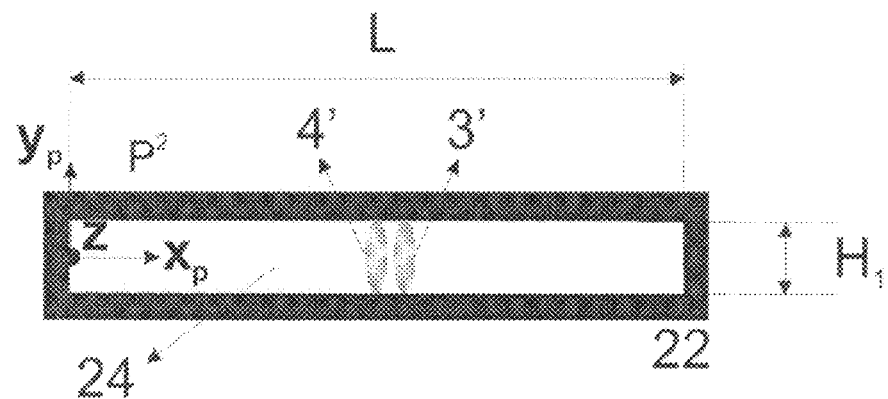
FIG. 12a illustrates a device for delimiting the field of view of the detecting means to both directly reemitted and scattered light according to an embodiment of the invention.

A solution to allow passage of selected parts of light 5 received by the detecting means 20 in an inspection system 1 according to any of the embodiments is shown in FIGS. 12a,b and c. The device 22 is a diaphragm device having a slit-like aperture 24. The dimensions of the aperture 24 are selected in correspondence the dimensions of said image 3' or components thereof as obtained by the focusing means 21 to yield the specified field of view. The aperture 24 can be formed as a rectangular opening in a plate but can also be a rectangular region in a plate, this region being transmissive to substantially only the wavelength or range of wavelengths of the light originating from the scanned product stream 2 while the remainder of the plate will block any light. In another embodiment the element 22 can be a bitmap stored in an electronic memory or can be implemented as the filtering function w in software.

The diaphragm 22 is by definition a sub-region of said imaging plane $P^2$. This plane $P^2$ substantially coincides with the image plane of focus of the detection means 20. The aperture opening 24 is aligned along the projected scan line $S_p$. The field-of-view delimiting characteristics of diaphragm 22 are fully described by a one-dimensional spatial filtering function or window w dependent only on the direction $y_p$. The field delimiting devices 22 is universally applicable to any of the image types (striped, circular or elliptical), more specifically any image having a linear character and obtained by an inspection system 1 according to any embodiment of the invention.

FIG. 12a illustrates a device 22 for delimiting the field of view of the detecting means 20 to both directly reemitted light 7 and scattered light 8 according to an embodiment of the invention. The aperture 24 is shaped as a rectangle, the length L along the $x_p$-axis thereof is preferably such that the total length d of the active area of the conversion means 25 is used. The height $H_1$ along the $y_p$-axis thereof is preferably chosen to be substantially proportional to or more than the overall height $K_1$ of the image 3' in $P^2$. The characteristic window function w then becomes $$w_1(y_p) = \begin{cases} 0, & |y_p| \geq \frac{H_1}{2} \\ 1, & |y_p| < \frac{H_1}{2}. \end{cases}$$

Figure 12B:
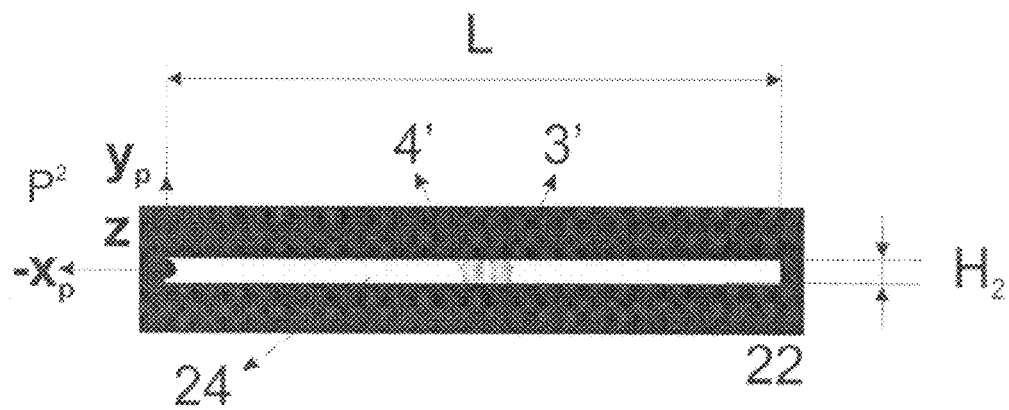
FIG. 12b illustrates a device for delimiting the field of view of the detecting means to substantially only directly reemitted light according to an embodiment of the invention.

FIG. 12b illustrates a device 22 for delimiting the field of view of the detecting means 20 to predominantly only directly reemitted light 7 according to an embodiment of the invention. The aperture 24 is shaped as a rectangle, the length L along the $x_p$-axis thereof is preferably such that the total length d of the active area of the conversion means 25 is used, the height $H_2$ along the $y_p$-axis thereof being substantially proportional to the height $K_2$ of the component of the image 3' in $P^2$, this component being representative of the collected directly reemitted light 7. As shown inter alia in FIGS. 10 and 11 this component corresponds to the middle part of the image 3' formed. Due to the magnification provided by the focusing means 21 at least in the direction $y_p$, the dimension $K_2$ of this directly reemitted component can be extended. Hence the dimensions $K_2$ of the directly reemitted component 7 of the image 3' can differ from the diameter of the scanning light beam 14. The height $H_2$ of the aperture 24 can thus be selected in a range which allows manufacturing optimizations of the diaphragm. The characteristic window function w then becomes $$w_2(y_p) = \begin{cases} 0, & |y_p| < \frac{H_2}{2} \\ 1, & |y_p| \geq \frac{H_2}{2}. \end{cases}$$

Figure 12C:
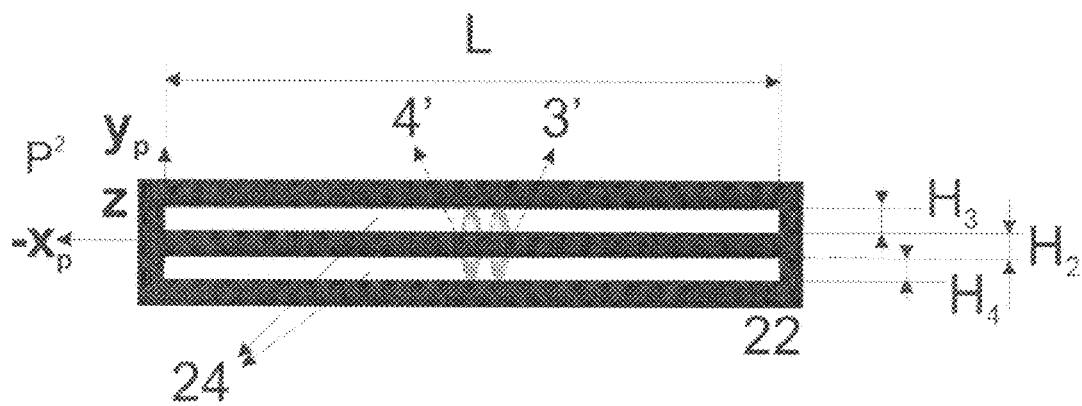
FIG. 12c illustrates a device for delimiting the field of view of the detecting means to substantially only scattered light according to an embodiment of the invention.

FIG. 12c illustrates a device 22 for delimiting the field of view of the detecting means 21 to substantially only scattered 8 light according to an embodiment of the invention. The aperture 24 is shaped as two spaced apart rectangles, the length L along the $x_p$-axis thereof is preferably such that the total length d of the active area of the conversion means 25 is used, the spacing $H_2$ along the $y_p$-axis between the two rectangles thereof being substantially proportional to the height $K_2$ of the component of the image 3' in $P^2$, this component corresponding to the directly reemitted light 7. This spacing will block the passage of the middle part of the image 3'. As shown inter alia in FIGS. 10 and 11 this component corresponds to the middle part of the image 3' formed. Due to the magnification provided by the focusing means 21 at least in the direction $y_p$ the dimension $K_2$ of this directly reemitted light 7 component can be extended. Hence the dimension $K_2$ of the directly reemitted light component on the image 3' can differ from the diameter of the scanning light beam 14. The spacing $H_2$ between the two rectangles constituting the aperture 24 can thus be in a range which allows manufacturing optimizations of the diaphragm. The heights $H_3$ and $H_4$ are preferably chosen to be substantially proportional to the heights $K_3$ and $K_4$ of the outer parts of the image 3', this parts corresponding to the component related to scattered light 8. Due to the magnification provided by the focusing means 21 at least in the direction $y_p$ the dimensions $K_3$ and $K_4$ of this scattered component 8 can be extended. Hence the dimensions $H_3$ and $H_4$ of the windows allowing passage of only the scattered 8 component of the image 3' can thus be in a range which allows manufacturing optimizations of the diaphragm. The characteristic window function then becomes $$w_3(y_p) = \begin{cases} 0, & |y_p| < \frac{H_2}{2} \\ 1, & \frac{H_3}{2} \geq |y_p| \geq \frac{H_2}{2} \\ 0, & |y_p| > \frac{H_3}{2}, \end{cases}$$

assuming $H_3=H_4$.

Devices 22 other than diaphragms can be used to determine the field of view of the detecting means 20. One can for example select the magnification of the focusing means 21 such that detecting means 20 is sensitive to predominantly only directly reemitted light 7. As the focusing means 21 provide magnification at least in the direction $y_p$, the height $K_2$ of the inner part of the image 3' corresponding to directly reemitted light 7 can be increased such that the outer parts of the image 3' corresponding to the scattered 8 light is further downstream directed outside the active area of the conversion means 25. Hence these outer parts can not be converted by the conversion means 25 and an electrical signal representative of predominantly only directly reemitted light 7 is obtained.

The characteristic window function w can take other forms apart from the ones given above. For instance a Gaussian function along $y_p$ can be suitable as well, likewise other windowing functions can be tailored to the application at hand, as can be appreciated by a person skilled in the art.

When sorting products, electrical signals are to be generated proportional to predominantly directly reemitted light 7, scattered light 8, transmitted light or any light originating from the scanned product 3 and subsequently collected and received 5 by the detecting means 20. These electrical signals can be separately processed, e.g. amplified. Optionally electrical signals are generated which are a combination of any of the above light signals. An inspection system 1 according to any of the embodiments can thus further comprise conversion means 25 for converting the detected light 5 into an electrical signal. Optionally a light pipe or a small focusing lens (not shown) is positioned in between the delimiting device 22 and the conversion means 25 to guide or direct the light towards said conversion means 25.

Preferably the analogue electrical signal of the conversion means is transformed into a digital signal using known analogue-to-digital converters. As stated supra an inspection system 1 according to any of the embodiments can also further comprise control circuitry in operable communication with the detecting means 20 for receiving these electrical signals. The control circuitry will then generate control signals based on individual electrical signals or a combination of any of these electrical signals. Any mathematical operation can be applied upon the electrical signals using known electronic circuitry and electronic data processing equipment. The signals can be manipulated by the control circuitry e.g. being summed, subtracted, multiplied or otherwise processed in any known manner.

As the light 5 received by the detecting means 20 doesn't pass via the scanning means 21, the amount of light receivable by the detecting means 20 can be higher or the noise can be lower than in the prior inspection systems using a rotating polygon wheel. The conversion means 25 can be any high efficient conversion means used in prior art inspection systems such as a photo-electrical device or photomultiplier tube. As the detecting means 20 can be adjusted to increase the amount of light received 5 by the detecting means 20 independent from the scanning means 10, also less efficient conversion means 25 such as avalanche diodes can be used to convert the optical signals into electrical signals. The conversion means 25 can be a charge-coupled-device such as a CCD-camera or CMOS image sensor which operate at sufficient scan rates when enough light is available.

Using a conversion means 25 comprising an array of individually addressable light sensitive elements or pixels, one has the advantage to delimit the field of view of the detecting means 20 by only selecting and reading-out those pixels corresponding to the predominantly directly reemitted light 7 component, to the scattered light 8 component or to both components of the image 3' formed by the focusing means 21 in $P^2$. Alternatively such a pixel-array allows a flexible definition of the delimiting element 22 implemented in software or hardware, more particularly an algorithmic implementation of the characterizing window function w.

Figure 13:
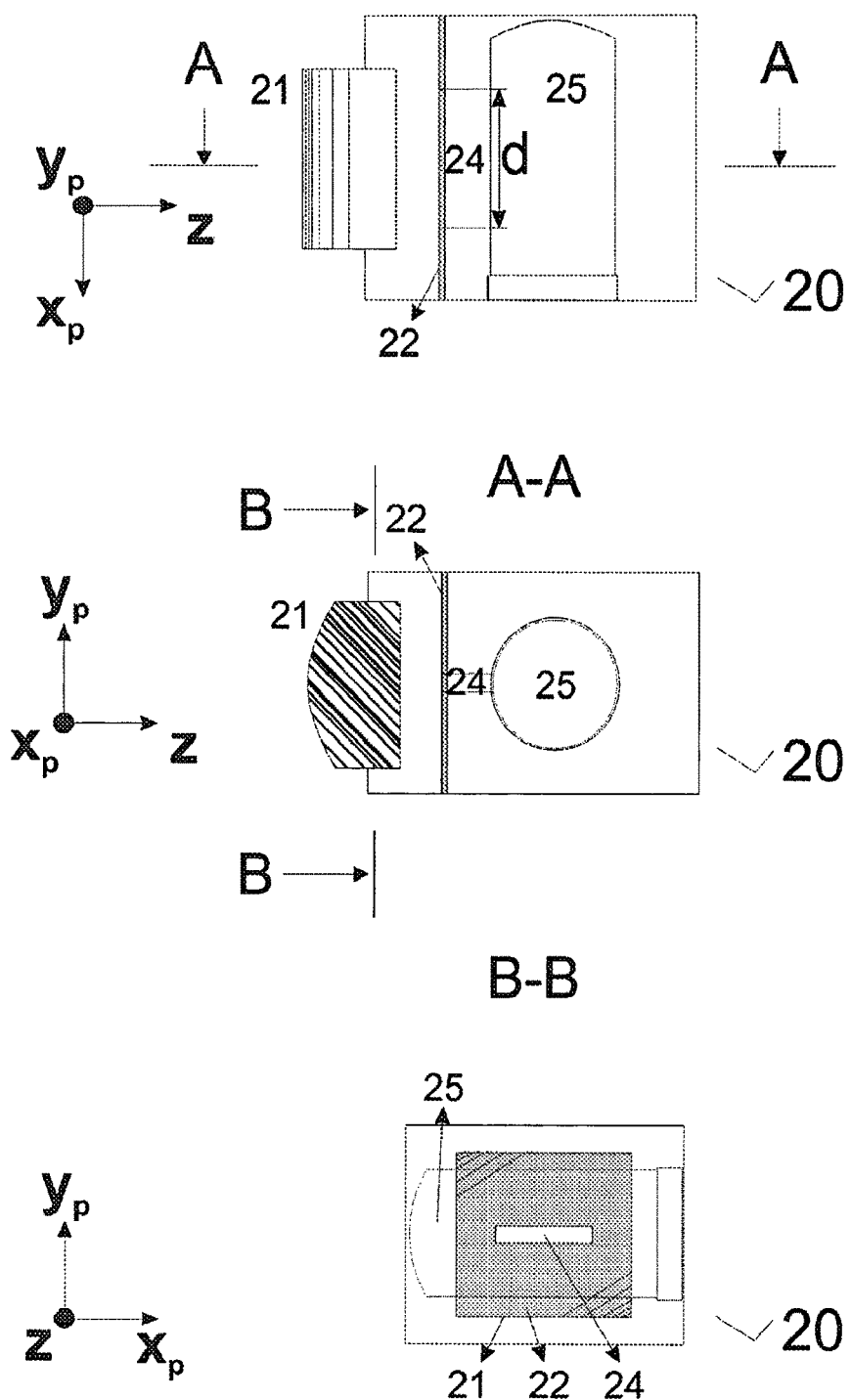
FIG. 13 shows a top view (top), a side view along section A-A (middle) and a frontal view along section B-B (bottom) of a detecting means according to a preferred embodiment comprising a cylindrical lens as focusing means, a device for delimiting the field of view of the detecting means to substantially only the directly reemitted light and a photoelectrical device according to an embodiment of the invention.

FIG. 13 shows a top view (top), a side view along section A-A (middle) and a frontal view along section B-B (bottom) of a detecting means 20 according to a preferred embodiment comprising a cylindrical lens as focusing means 21 focusing and magnifying the incoming light beams 5 only in the direction $y_p$, a diaphragm device 22 having a slit aperture 24 for delimiting the field of view of the detecting means 20 to predominantly only the directly reemitted light 7, the diaphragm device 22, being positioned in between the focusing means 21 and the conversion means 25 and a photoelectrical device 25 for converting the component representative of the directly reemitted light 7 into an electrical signal. FIG. 13 illustrates that the longitudinal aperture 24 of the diaphragm 22 and the active area of the conversion means 25 are aligned with the direction $x_p$ along the projected scan line $S_p$ in $P^2$ and extends either because in use the object 3 is projected as a stripped image along said $x_p$ direction or it moves during scanning along said $x_p$ direction. This $x_p$ direction is along the axis meridian and the direction $y_p$ along the power meridian of said cylindrical lens 23. It will be appreciated by a person skilled in the art that similar embodiments fall within the scope of the invention, such as those having different field of views, different conversion means 25, different optical configurations to further improve the signal/noise ratio, spherical- and chromatic aberrations or field curvature etc.

Figure 14:
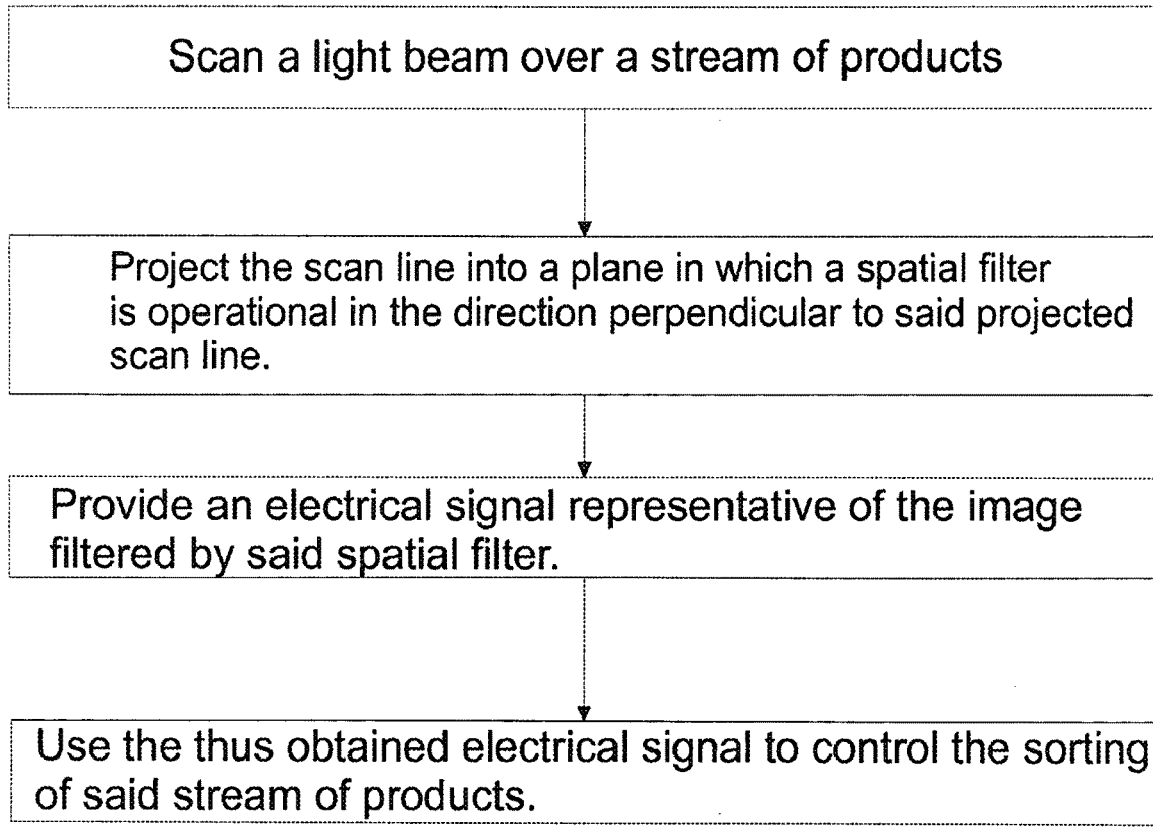
FIG. 14 is a flowchart illustrating steps of a method for inspecting a stream of products using a scanning light beam according to embodiments of the invention.

FIG. 14 is a flowchart illustrating the steps of a method for inspecting a stream of products 2 using a concentrated light beam 14 according to embodiments of the invention. A concentrated light beam 14 provided by scanning means 10 is cast over the product stream 2 to scan objects 3 contained therein. Upon scanning, light will be directly reemitted 7' and/or scattered 8' by the scanned objects 3. Part of the directly reemitted light 7' and the scattered light 8' will be received by the detecting means 20 which are positioned to receive light returning from the scanned product stream 2, i.e. light 5 that has not been directed back towards the scanning means 10. The received light 5 is then focused to provide an image 3' in the plane $P^2$, said image 3' being either a striped image or a moving image along the projected scan line $S_p$. The image 3' is spatially filtered in $P^2$ by a filter characterized by a window function w dependent only on the direction $y_p$ perpendicular to said projected scan line $S_p$. Based upon this filtered image an electrical signal is provided representative of predominantly the directly reemitted light 7 component, the scattered light 8 component or both components in the original image. This electrical signal can then be used to generate control signals for controlling the sorting of the scanned objects 3 from the product stream 2.

The inspecting system 1 and method according to any of the embodiments is of particular use in an apparatus for sorting products. A sorting apparatus can contain more than one inspecting system according to the invention. Such sorting apparatus are known in the art. Typically a sorting apparatus comprises a supply system for transporting and guiding products 3 to the inspection system 1 for inspection thereof. The sorting apparatus can further comprise a removal system for removing after inspection rejected products or unwanted objects from the product stream 2.

Such transport and guiding system can comprise a conveyor, a vibrating table or shaker for transporting the products, a chute 31 for guiding the free fall of the products towards the inspection system. It is known in the art to use compressed air for removing products from the product stream. The removal system then comprises multiple nozzles for blowing compressed air towards the rejected products when passing in front of one of these nozzles. Alternatively fingers or flaps can be used to eject unwanted objects out of the product stream 2 as is well known by the person skilled in the art.

It is thus advantageous to equip a sorting apparatus with an inspection system according to any embodiments of the invention as the overall performance of the sorting apparatus can be improved significantly e.g. thanks to the flexible configuration of the inspection system and by the independent optimization of the detecting means and the scanning means.

The invention claimed is:

1. An inspection system for inspecting irregular objects in a stream of products based on forming a scan line by means of at least one light source, directing light along the scan line, and measuring scattered light or directly reemitted light obtained from objects in the illuminated product stream; the inspection system comprising:

means for scanning the stream of products along the scan line, the scanning means comprising a focusing means for concentrating the light in at least one dimension;

a detecting means configured to detect light beams reemitted by the product stream upon scanning, which detection means produces an electrical signal proportional to the detected light beams;

the detecting means comprising a focusing means defining an image plane for forming a spatial image of the stream of products along the scan line, the focusing means being configured to focus the image in at least one dimension and being oriented towards the scan line such that points on the scan line form a projected scan line along a direction $x_p$ in the image plane, and the detecting means further comprising a spatial filtering means operating in the image plane, the spatial filtering means being configured to filter the image in substantially only the direction perpendicular to the direction of the projected scan line such that a field of view of the detecting means is delimited to predominantly directly reemitted light or predominantly scattered light.

2. The inspection system according to claim 1, wherein the light source is a laser beam generator emitting concentrated light over the scan line.

3. The inspection system according to claim 1, wherein the scanning means comprises a multifaceted polygonal mirror for directing a light beam along the scan line.

4. The inspection system according to claim 1, wherein the scanning means comprises an array of light sources sequentially or permanently directing light beams along the scan line.

5. The inspection system according to claim 1, wherein the scanning means comprises more than one light source having different wavelengths.

6. The inspection system according to claim 1, wherein the focusing means comprises at least one focusing lens for forming the image substantially focused in at least one dimension.

7. The inspection system according to claim 6, wherein the at least one focusing lens is selected from the group consisting of cylindrical, spherical and aspherical lenses such that a converging lens system focuses incoming light in at least one dimension.

8. The inspection system according to claim 1, wherein the focusing means of the scanning means comprises at least one optical device selected from the group consisting of a lens, a beamer, a grating and a collimating device for generating a static sheet of concentrated light.

9. The inspection system according to claim 1, wherein the filtering means is a diaphragm device positioned in the image plane and having a slit aperture, or bitmap stored in a memory.

10. The inspection system according to claim 9, wherein the filtering means have an aperture configured as a rectangle, the rectangle having a height equal to or more than the height of the image to provide sensitivity of the detecting means to both directly reemitted and scattered lights.

11. The inspection system according to claim 9, wherein the filtering means have an aperture configured as a rectangle, the rectangle having a height equal to or less than the height of the image corresponding to the predominantly directly reemitted light to provide sensitivity of the detecting means to predominantly directly reemitted light.

12. The inspection system according to claim 9, wherein the filtering means has two apertures configured as rectangles spaced apart from each other, the spacing between the apertures being substantially equal to the height of the image corresponding to the predominantly directly reemitted light whereby the detecting means is made sensitive to scattered light.

13. The inspection system of claim 1, wherein at least one detecting means and the scanning means are located at a same side relative to the product stream such that the detection is conducted using reflected light from the product stream.

14. The inspection system of claim 1, wherein at least one of the detecting means and the scanning means are located at opposite sides relative to the product stream such that the detection is conducted using the light transmitted through the product stream.

15. The inspection system of claim 1, wherein at least one of the detecting means is located at a same side and at least one of the detecting means is located at an opposite side with the scanning means such that the detection is carried out using on a combination of both reflected light from the product stream and light transmitted through the product stream.

16. The inspection system according to claim 1, wherein the detecting means further comprises conversion means for converting the detected optical signals into an electrical signal.

17. The inspection system according to claim 16, wherein the conversion means is selected from the group consisting of photo-electrical devices, photomultiplier diodes, avalanche diodes, arrays of photomultiplier tubes, charge-coupled devices, CCD camera chips and CMOS image sensors.

18. A method for inspecting and sorting objects in a stream of products, the method comprising the step of using the inspection system according to claim 1 in a sorting apparatus.

19. A sorting apparatus for detecting and removing unsuitable or irregular objects in a stream of products based on forming of a scan line by means of at least one light source directing light along the scan line, and measuring scattered light or directly reemitted light obtained from the objects in the illuminated product stream; the apparatus comprising:

an inspection system comprising means for scanning the stream of products along the scan line, and the scanning means comprising a focusing means for concentrating the light in at least one dimension; and a detection means configured for detecting light beams reemitted by the product stream upon scanning, which detection means produces an electrical signal proportional to the detected light beams, a supply system for transporting the product stream towards the inspection system, a control circuit processing the electrical signals from the detection means of the inspection system and converting the electrical signals into a corresponding control signal, and a removal unit operated in accordance with the control signals of the control circuitry;

the detecting means comprising a focusing means defining an image plane in which a spatial image of the stream of products along the scan line is formed, the focusing means being configured to focus the image in at least one dimension and being oriented towards the scan line such that the points on the scan line form a projected scan line along a direction $x_p$ in the image plane, and the detecting means further comprising a spatial filtering means operating in the image plane, which spatial filtering means filter the image in substantially only the direction perpendicular to the direction of the projected scan line such that the field of view of the detecting means is delimited to predominantly directly reemitted light or predominantly scattered light.

20. The sorting apparatus according to claim 19, wherein the inspection system comprises at least two of the filtering means for generating electrical signals based on both directly reemitted and scattered lights, only predominantly directly reemitted light and/or only scattered light, the at least two of the filtering means selected from the group consisting of:

an aperture configured as a rectangle, the height thereof being equal to or more than the height of the image such that the detecting means is sensitive to both directly reemitted and scattered lights;

an aperture configured as a rectangle, the height thereof being equal to or less than the height of the image corresponding to the predominantly directly reemitted light to provide a sensitivity of the detecting means to predominantly directly reemitted light;

two apertures spaced apart from each other, said spacing between the apertures being substantially equal to the height of the image corresponding to the predominantly directly reemitted light whereby the detecting means is made sensitive to only scattered light.

21. The sorting apparatus according to claim 19, wherein the control circuitry is configured to receive the electrical signals and generate a control signal depending on either of the electrical signals representative of both directly reemitted and scattered lights, only predominantly directly reemitted light, only scattered light, or combinations thereof.

22. The sorting apparatus of claim 19, wherein the apparatus further comprises a removal unit which is an array of air ejectors operated with the control signals of the control circuitry.

23. A method for inspecting and sorting objects in a stream of products, the method comprising the steps of;
   a) scanning the stream of products along a scan line, the scan line being formed by means of at least one light source directing a concentrated light along the scan line,
   b) focusing light beams reemitted by the product stream in at least one dimension and forming a focused image in an image plane such that points on the scan line forming a projected scan line along a direction $x_p$ in the image plane,
   c) spatially filtering the image substantially located in the image plane with a spatial filtering means in substantially only the direction perpendicular to the direction of the projected scan line such that passage of predominantly directly reemitted component or predominantly scattered component of the image is allowed to pass through the filtering means,
   d) obtaining optical signals received from the filtered image and generating electrical signals representative of both directly reemitted and scattered lights and/or only predominantly directly reemitted light and/or only scattered light, and
   e) receiving the electrical signal(s) of the previous step and generating control signal(s) based on either of both directly reemitted light and scattered light, only predominantly directly reemitted light, only scattered light or combinations thereof.

24. The method according to claim 23, wherein the predominantly directly reemitted light and scattered light are the lights that are either reflected or transmitted by the product stream.

25. The method according to claim 23, wherein the sorting of unsuitable objects is carried out based on color, structure or combination thereof.

26. The method according to claim 23, wherein the method further comprises scanning the stream of products with at least two light sources having different wavelengths.

27. The method according to claim 23, wherein unsuitable objects from the product stream are removed by a removal unit based on the control signal(s).

* * * * *